US006673332B1

(12) United States Patent
Goldstein et al.

(10) Patent No.: US 6,673,332 B1
(45) Date of Patent: Jan. 6, 2004

(54) ASSAYS FOR INHIBITORS OF NEURONAL TRANSPORT OF ALZHEIMER'S AMYLOID PRECURSOR PROTEIN

(75) Inventors: Lawrence S. B. Goldstein, San Diego, CA (US); Adeela Kamal, San Diego, CA (US); Gorazd Stokin, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/724,880

(22) Filed: Nov. 28, 2000

Related U.S. Application Data
(60) Provisional application No. 60/252,623, filed on Nov. 22, 2000.

(51) Int. Cl.[7] .................... A61K 49/00; G01N 33/543; G01N 33/536
(52) U.S. Cl. ................ 424/9.2; 436/518; 436/536
(58) Field of Search ............... 424/9.2; 436/536, 436/518; 530/412; 204/450; 435/5, 7.1, 500

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,946,778 A | 8/1990 | Ladner et al. | |
| 4,965,188 A | 10/1990 | Mullis et al. | |

FOREIGN PATENT DOCUMENTS

WO  PCT US98/18368  3/1990

OTHER PUBLICATIONS

Perl, "Relationship of Aluminum to Alzheimer's Disease," *Environmental Health Perspective* 63:149 [1985].
Perl et al., "Alzheimer's Disease: X–ray Spectrometric Evidence of Aluminum Accumulation in Neurofibrillary Tangle–Bearing Neurons," *Science* 208:297 [1980].
Shoji et al., "Production of the Alzheimer Amyloid β Protein by Normal Proteolytic Processing," *Science* 258:126 [1992].
Kosik, "Alzheimer's Disease: A Cell Biological Perspective," *Science* 256:780 [1992].
Mattson et al., "β–Amyloid Peptides Destabilize Calcium Homeostatis and Render Human Cortical Neurons Vulnerable to Excitotoxicity," *J. Neuroscience* 12:376 [1992].
Haass and Selkoe, "Cellular Processing of β–Amyloid Precursor Protein and the Genesis of Amyloid β–Peptide," *Cell* 75:1039 [1993].
Teller et al., "Presence of soluble amyloid β–peptide precedes amyloid plaque formation in Down's syndrome," *Nature Med.*, 2:93 [1996].
Köhler and Milstein, "Continuous cultures of fused cells secreting antibody of predefined specificity," *Nature* 256:495–497 [1975].
Kozbor et al. "The production of monoclonal antibodies from human lymphocytes," *Immunol. Today* 4:72 [1983].
Cole et al., "The EBV–Hybridoma Technique and Its Application to Human Lung Cancer," in *Monoclonal Antibodies and Cancer Therapy*, Alan R. Liss, Inc., pp 77–96 [1985].
Cote et al., "Generation of human monoclonal antibodies reactive with cellular antigens," *Proc. Natl. Acad. Sci. U.S.A.* 80:2026–2030 [1983].
Huse et al., "Generation of a Large Combinatorial Library of the Immunoglobulin Repertoire in Phage Lambda," *Science* 246:1275–1281 [1989].
Sambrook et al., *Molecular Cloning: A Laboratory Manual*, Cold Spring Harbor Press, NY, pp 9.31–9.58 [1989].
Sambrook et al., *Molecular Cloning: A Laboratory Manual*, Cold Spring Harbor Press, NY, pp 7.39–7.52 [1989].
Crowther, "Enzyme–Linked Immunosorbent Assay (ELISA)," in *Molecular Biomethods Handbook*, Rapley et al. [eds.], pp. 595–617, Humana Press, Inc., Totowa, NJ [1998].
Harlow and Lane (eds.), *Antibodies: A Laboratory Manual*, Cold Spring Harbor Laboratory Press [1988].
Ausubel et al. (eds.), *Current Protocols in Molecular Biology*, Ch. 11, John Wiley & Sons, Inc., New York [1994].
Anderson and Young, "Quantitative Filter Hybridization," in *Nucleic Acid Hybridization* [1985].
Maniatis et al., "Regulation of Inducible and Tissue–Specific Gene Expression," *Science* 236:1237 [1987].
Sambrook et al., *Molecular Cloning: A Laboratory Manual*, 2nd ed., Cold Spring Harbor Laboratory Press, New York, pp. 16.7–16.8 [1989].
Selkoe, "Translating cell biology into therapeutic advances in Alzheimer's disease," *Nature* 399 (Suppl) A23–30 [1999].
Sinha and Lieberburg, "Cellular mechanisms of β–amyloid production and secretion," *Proc. Natl. Acad. Sci. USA* 96:11049–11053 [1999].
De Strooper and Annaert, "Proteolytic processing and cell biological functions of the amyloid precursor protein," *J. Cell. Sci.*, 113:1857–1870 [2000].
Koo et al., "Precursor of amyloid protein in Alzheimer disease undergoes fast anterograde axonal transport," *Proc. Natl. Acad. Sci. USA* 87:1561–1565 [1990].
Sisodia et al., "Identification and Transport of Full–Length Amyloid Precursor Proteins in Rat Peripheral Nervous System," *J. Neurosci.*, 13:3136–3142 [1993].
Amaratunga et al., "Inhibition of Kinesin Synthesis In Vivo Inhibits the Rapid Transport of Representative Proteins for Three Transport Vesicle Classes into the Axon," *J. Neurochem.*, 64:2374–2376 [1995].

(List continued on next page.)

*Primary Examiner*—Gary Kunz
*Assistant Examiner*—Sharon Turner
(74) *Attorney, Agent, or Firm*—Medlen & Carroll LLP

(57) ABSTRACT

The present invention provides methods and compositions for the treatment of Alzheimer's disease. In particular, the present invention provides methods and compositions suitable to assess, characterize, and identify inhibitors of neuronal transport of Alzheimer's amyloid precursor protein.

13 Claims, 9 Drawing Sheets

OTHER PUBLICATIONS

Ferreira et al., "Intraneuronal Compartments of the Amyloid Precursor Protein," J. Neurosci., 12:3112–3123 [1993].

Kaether et al., "Axonal Membrane Proteins Are Transported in Distinct Carriers: A Two–Color Video Microscopy Study in Cultured Hippocampal Neurons," Mol. Biol. Cell 11:1213–1224 [2000].

Yamazaki et al., "Trafficking of Cell Surface β–Amyloid Precursor Protein: Retrograde and Transcytotic Transporter in Cultured Neurons," J. Cell. Biol., 129:431–442 [1995].

Brady, "A novel brain ATPase with properties expected for the fast axonal transport motor," Nature 317:73–75 [1985].

Vale et al., "Identification of a Novel Force–Generating Protein, Kinesin, Involved in Microtubule–Based Motility," Cell 42:39–50 [1985].

Goldstein and Philip, "The Road Less Traveled: Emerging Principles of Kinesin Motor Utilization," Ann. Rev. Cell Dev. Biol., 15:141–183 [1999].

Goldstein and Yang, "Microtubule–Based Transport Systems in Neurons: The Roles of Kinesins and Dyneins," Ann. Rev. Neurosci., 23:39–72 [2000].

Kamal and Goldstein, "Connecting vesicle transport to the cytoskeleton," Curr. Opin. Cell Biol., 12:503–508 [2000].

Rahman et al., "Defective Kinesin Heavy Chain Behavior in Mouse Kinesin Light Chain Mutants," J. Cell. Biol., 146:1277–1288 [1998].

Xia et al., "Chromosomal Localization Reveals Three Kinesin Heavy Chain Genes in Mouse," Genomics 52:209–231 [1999].

Yang et al., "A Three–Domain Structure of Kinesin Heavy Chain Revealed by DNA Sequence and Microtubule Binding Analyses," Cell 56:879–889 [1989].

de Cuevas et al., "Evidence That the Stalk of Drosophila Kinesin Heavy Chain Is an α–Helical Coiled Coil," J. Cell Biol., 116:957–965 [1992].

Gauger and Goldstein, "The Drosophila Kinesin Light Chain," J. Biol. Chem., 268:13657–13666 [1990].

Hirokawa et al., "Submolecular Domains of Bovine Brain Kinesin Identified by Electron Microscopy and Monoclonal Antibody Decoration," Cell 056:867–878 [1989].

Bi et al., "Kinesin– and Myosin–driven Steps of Vesicle Recruitment for $Ca^{2+}$–regulated Exocytosis," J. Cell. Biol., 138:999–1008 [1997].

Seiler et al., "Cargo binding and regulatory sites in the tail of fungal conventional kinesin," Nat. Cell Biol., 2:333–338 [2000].

Skoufias et al., "The Carboxyl–terminal Domain of Kinesin Heavy Chain Is Important for Membrane Binding," J. Biol. Chem., 269:1477–1485 [1994].

Coy et al., "Kinesin's tail domain is an inhibitory regulator of the motor domain," Nat. Cell Biol., 1:288–292 [1999].

Friedman and Vale, "Single–molecule analysis of kinesin motility reveals regulation by the cargo–binding tail domains," Nat. Cell Biol., 1:293–297 [1999].

Hackney and Stock, "Kinesin's IAK tail domain inhibits microtubule–stimulated ADP release," Nat. Cell Biol., 2:257–260 [2000].

Stock et al., "Formation of the Compact Conformer of Kinesin Requires a COOH–terminal Heavy Chain Domain and Inhibits Microtubule–stimulated ATPase Activity," J. Biol. Chem., 274:14617–14623 [1999].

Diefenbach et al., "The C–Terminal Region of the Stalk Domain of Ubiquitous Human Kinesin Heavy Chain Contains the Binding Site for Kinesin Light Chain," Biochem., 37:16663–16670 [1998].

Gindhart and Goldstein, "Tetratrico peptide repeats are present in the kinesin light chain," Trends Biochem. Sci., 21:52–53 [1996].

Lamb et al., "Tetratrico peptide repeat interactions: to TPR or not to TPR?," Trends Biochem. Sci., 20:257–259 [1995].

Blatch and Lassie, "The tetratricopeptide repeat: a structural motif mediating protein–protein interactions," Bioessays 21:932–939 [1999].

Kumar et al., "Kinectin, an Essential Anchor for Kinesin––Driven Vesicle Motility," Science 267:1834–1837 [1995].

Toyoshima et al., "Kinectin, a Major Kinesin–binding Protein on ER," J. Cell Biol., 118:1121–1131 [1992].

Toyoshima and Sheetz, "Kinectin distribution in chicken nervous system," Neurosci. Lett., 211:171–174 [1996].

Tai et al., "Rhodopsin's Carboxy–Terminal Cytoplasmic Tail Acts as a Membrane Receptor for Cytoplasmic Dynein by Binding to the Dynein Light Chain Tctex–1," Cell 97:877–887 [1999].

Okada et al., "The Neuron–Specific Kinesin Superfamily Protein KIF1 A Is a Unique Monomeric Motor for Anterograde Axonal Transport of Synaptic Vesicle Precursors," Cell 81:769–780 [1995].

Zheng et al., "PAT1, a microtubule–interacting protein, recognizes the basolateral sorting signal of amyloid precursor protein," Proc. Natl. Acad. Sci. USA 95:14745–14750 [1995].

Torroja et al., "Neuronal overexpression of APPL, the Drosophila homologue of the amyloid precursor protein (APP), disrupts axonal transport," Curr. Biol., 9:489–492 [1999].

Gindhart et al., "Kinesin Light Chains Are Essential for Axonal Transport in Drosophila," J. Cell Biol., 141:443–452 [1998].

Hurd and Saxton, "Kinesin Mutations Cause Motor Neuron Disease Phenotypes by Disrupting Fast Axonal Transport in Drosophila," Genetics 144:1075–1085 [1996].

Hurd et al., "Mutation of the Axonal Transport Motor Kinesin Enhances paralytic and Suppressor Shaker in Drosophila," Genetics 142:195–204 [1996].

Bowman et al., "Drosophila roadblock and Chlamydomonas LC7: A Conserved Family of Dynein–associated Proteins Involved in Axonal Transport, Flagellar Motility, and Mitosis," J. Cell. Biol., 146:165–179 [1999].

Martin et al., "Cytoplasmic Dynein, the Dynactin Complex, and Kinesin Are Interdependent and Essential for Fast Axonal Transport," Mol. Biol. Cell, 10:3717–3728 [1999].

Ikin et al., "Alzheimer Amyloid Protein Precursor Is Localized in Nerve Terminal Preparations to Rab5–containing Vesicular Organelles Distinct from Those Implicated in the Synaptic Vesicle Pathway," J. Biol. Chem., 271:31783–31786 [1996].

Otsuka et al., "The C. elegans unc–104 Gene Encodes a Putative Kinesin Heavy Chain–like Protein," Neuron 6:113–122 [1991].

Yonekawa et al., "Defect in Synaptic Vesicle Precursor Transport and Neuronal Cell Death in KIF1 A Motor Protein–deficient Mice," J. Cell Biol., 141:431–441 [1998].

Rubin et al., "Comparative Genomics of the Eukaryotes," Science 287:2204–2215 [2000].

Scheufler et al., "Structure of TPR Domain–Peptide Complexes: Critical Elements in the Assembly of the Hsp70–Hsp90 Multichaperone Machine," *Cell* 101:199–210 [2000].

Stenoien et al., "Immunochemical Analysis of Kinesin Light Chain Function," *Mol. Biol. Cell*, 8:675–689 [1997].

Steinberg and Schwila, "The Neurospora Organelle Motor: A Distant Relative of Conventional Kinesin with Unconventional Properties," *Mol. Biol. Cell*, 6:1605–1618 [1995].

Verhey et al., "Light Chain–dependent Regulation of Kinesin's Interaction with Microtubules," *J. Cell Biol.*, 143:1053–1066 [1998].

Checler, "Processing of the β–Amyloid Precursor Protein and Its Regulation in Alzheimer's Disease," *Neurochem.*, 65:1431–1444 [1995].

Improper format cumulative PCT US98/18368.

Stites and Terr (1991) in *Basic and Clinical Immunology*, 7th ed., Appleton & Lange, Norwalk, Connecticut.

Maggio (1980) in *Enzyme Immunoassay*, CRC Press, Boca Raton, FL.

Tijssen (1985) "Practice and Theory of Enzyme Immunoassays," in *Laboratory Techniques in Biochemistry and Molecular Biology*, Elsevier Science Publishers, B.V. Amsterdam.

Collioud et al. (1993) "Oriented and Covalent Immobilization of Target Molecules to Solid Supports: Synthesis and Application of a Light–Activatable and Thiol–Reactive Cross–Linking Reagent," Bioconjugate Chem. 4:528–536.

Schuhmann et al. (1991) "Immobilization of Enzymes on Langmuir–Blodgett Films via a Membrane–Bound Receptor. Possible Applications for Amperometric Biosensors," Adv. Mater. 3:388–391.

Lu et al. (1995) "Oriented Immobilization of Fab' Fragments on Silica Surfaces," Anal. Chem. 67:83–87.

Iwane et al. (1997) "Myosin Subfragment–1 Is Fully Equipped with Factors Essential for Motor Function," Biophys. Biochem. Res. Comm. 230:76–80.

Ng et al., "Engineering Protein—Lipid Interactions: Targeting of Histidine–Tagged Proteins to Metal–Chelating Lipid Monolayers," Langmuir 11:4048–4055 [1995].

Schmitt et al., "Specific Protein Docking to Chelator Lipid Monolayers Monitored by FT–IR Spectroscopy at the Air–Water Interface," *Angew. Chem. Int. Ed. Engl.*, 35:317–320 [1996].

Frey et al. (1996) "Two–dimensional protein crystallization via metal–ion coordination by naturally occurring surface histidines," Proc. Natl. Acad. Sci. USA 93:4937–4941.

Kubalek et al. (1994) "Two–Dimensional Crystallization of Histidine–Tagged, HIV–1 Reverse Transcriptase Promoted by a Novel Nickel–Chelating Lipid," J. Struct. Biol. 113:117–123.

Sigal et al. (1996) "A Self–Assembled Monolayer for the Binding and Study of Histidine–Tagged Proteins by Surface Plasmon Resonance," Anal. Chem. 68:490–497.

Huang and Hackney, "Drosophila Kinesin Minimal Motor Domain Expressed in *Escherichia coli*," *J. Biol. Chem.*, 269:16493 [1994].

Sakowicz et al., "A Marine Natural Product Inhibitor of Kinesin Motors," *Science* 280:292–295 [1998].

Rahman et al., "Two Kinesin Light Chain Genes in Mice," *J. Biol. Chem.*, 273:15395–15403 [1999].

Mountford et al., "Dicistronic targeting constructs: Reporters and modifiers of mammalian gene expression," *Proc. Natl. Acad. Sci. USA* 91:4303–4307 [1994].

Wurst and Joyner, in Joyner (ed.), *Gene Targeting: A Practical Approach*, Oxford University Press, New York, [1993], pp. 32–61.

Niclas et al., "Cloning and Localization of a Conventional Kinesin Motor Expressed Exclusively in Neurons," *Neuron* 12:1059–1072 [1994].

Perez et al., "Mutagenesis Identifies New Signals for β–Amyloid Precursor Protein Endocytosis, Turnover, and the Generation of Secreted Fragments, Including Aβ42," *J. Biol. Chem.*, 274:18851–18856 [2000].

Martin and Ames, "A Method for Determining the Sedimentation Behavior of Enzymes: Application to Protein Mixtures," *J. Biol. Chem.*, 236:1372–1379 [1961].

Hackney et al., "Kinesin Undergoes to 9 S to 6 S Conformational Transition," *J. Biol. Chem.*, 267:8696–8701 [1992].

Hanlon et al., "Chracterization if KIFC2, A Neuronal Kinesin Superfamily Member in Mouse," *Neuron* 18:439–451 [1997].

Marszalek et al., "Novel Dendritic Kinesin Sorting Identified by Different Process Targeting of Two Related Kinesins: KIF21A and KIF21B," *J. Cell Biol.*, 145469–479 [1999].

Ferreira et al., "Suppression of Kinesin Expression in Cultured Hippocampal Neurons Using Antisense Oligonucleotides," *J. Cell Biol.*, 117:595–606 [1992].

Kamal et al., Neuron 28:449–459 [2000] Axonal Transport of Amyloid Precursor Protein Is Mediated by Direct Binding to the Kinesin Light Chain Subunit of Kinesin–1.

A

B

ASSAYS FOR INHIBITORS OF NEURONAL TRANSPORT OF ALZHEIMER'S AMYLOID PRECURSOR PROTEIN

The present invention claims benefit under 35 U.S.C. §119(e) to Provisional Patent Application Ser. No. 60/252,623, filed on Nov. 22, 2000, now abandoned, which is herein incorporated by reference in its entirety for all purposes.

The present invention was made with government support from the National Institutes of Health, Grant No. GM35252. The United States Government has certain rights in the invention.

FIELD OF THE INVENTION

The present invention provides methods and compositions for the treatment of Alzheimer's disease. In particular, the present invention provides methods and compositions suitable to assess inhibitors of neuronal transport of Alzheimer's amyloid precursor protein.

BACKGROUND OF THE INVENTION

Alzheimer's disease (AD) is the fourth most common cause of death in the United States. Presently, Alzheimer's disease is the third most expensive disease in the United States, with costs reaching approximately $100 billion each year for direct medical costs such as nursing home care, direct nonmedical costs such as in-home day care, and indirect costs such as lost patient and care giver productivity. Alzheimer's disease presently afflicts more than four million people, and this number is expected to double during the next forty years with the aging of the population. Alzheimer's disease is also the most common cause of chronic dementia, with approximately two million people in the United States having dementia. At present, it is estimated that approximately ten percent of the population older than 65 years of age have mild to severe dementia. This high prevalence, combined with the rate of growth of the elderly segment of the population, make dementia and particularly Alzheimer's disease, important public health concerns. Medical treatment (including diagnostic and screening methods, as well as treatment regimens) may have economic benefits by slowing the rate of cognitive decline, delaying institutionalization, reducing care giver hours, and improving quality of life.

Alzheimer's disease is a complex multigenic neurodegenerative disorder characterized by progressive impairments in memory, behavior, language, and visuospatial skills, ending ultimately in death. Hallmark pathologies of Alzheimer's disease include granulovascular neuronal degeneration, extracellular neuritic plaques with β-amyloid deposits, intracellular neurofibrillary tangles and neurofibrillary degeneration, synaptic loss, and extensive neuronal cell death. It is now known that these histopathologic lesions of Alzheimer's disease correlate with the dementia observed in many elderly people.

Research on Alzheimer's disease has led investigators down numerous avenues. Although many models have been proposed, no single model satisfactorily accounts for all neuropathologic findings; nor do these models satisfactorily account for the requirement of aging for disease onset. Cellular changes, leading to neuronal loss and the underlying etiology of the disease, remain unknown. Proposed causes include environmental factors (Perl, *Environmental Health Perspective* 63:149 [1985]), such as metal toxicity (Perl et al., *Science* 208:297 [1980]), defects in beta-amyloid protein metabolism (Shijo et al., *Science* 258:126 [1992]; Kosik, *Science* 256:780 [1992]), and abnormal calcium homeostasis and/or calcium activated kinases (Mattson et al., *J. Neuroscience* 12:376 [1992]). The mechanisms of disease progression are equally unclear. Considerable human genetic evidence has implicated alterations in production or processing of the human amyloid precursor protein (APP) in the etiology of the disease. However, despite intensive research, much remains to be determined regarding the etiology of Alzheimer's disease. Thus, there remains a need in the art for methods and compositions suitable for treatment of this complex disease.

SUMMARY OF THE INVENTION

The present invention provides methods and compositions for the treatment of Alzheimer's disease. In particular, the present invention provides methods and compositions suitable to assess inhibitors of neuronal transport of Alzheimer's amyloid precursor protein.

The present invention provides methods for identifying modulators of transport of amyloid precursor protein comprising the steps of: providing kinesin-I, amyloid precursor protein, and at least one test compound suspected of having modulating activity; combining kinesin-I, amyloid precursor protein, and the test compound(s) under conditions such that the kinesin-I and amyloid precursor protein will bind to produce a kinesin-I/amyloid precursor protein complex, in the absence of an inhibitor. In preferred embodiments, the binding of the kinesin-I and amyloid precursor protein is detected. In some embodiments, the TPR domain of the light chain of kinesin-I interacts with the amyloid precursor protein. In some preferred embodiments, the binding of the kinesin-I and amyloid precursor protein is inhibited, while in other preferred embodiments, the binding of the kinesin-I and amyloid precursor protein is enhanced. In some embodiments, the binding is detected using any method suitable for the detection of such binding. In some embodiments, the methods used include, but are not limited to co-immunoprecipitation methods, co-immunoprecipitation followed by Western blotting, sucrose gradient centrifugation, microtubule binding assays, column chromatography methods, gel overlays, ATPase assays, and surface plasmon resonance (e.g., BIACORE). In some particularly preferred embodiments, the method comprises a co-immunoprecipitation method. In alternative embodiments, the method further comprises Western blotting. In still further embodiments, the methods involve microtubule binding assays, while in other embodiments, the methods involve ATPase assays, and in additional embodiments, the methods involve sucrose gradient centrifugation. In some preferred embodiments, biochemical methods are used. In alternative preferred embodiments, the method is conducted in vivo. In some preferred in vivo methods, the methods are conducted within cells, while in other embodiments, the methods are conducted within an animal (e.g., an animal model of disease). In some embodiments, the methods further comprise the step of exposing an animal to the complex of kinesin-I and amyloid precursor protein. In still further embodiments, the methods are conducted in vitro. The present invention further provides compounds identified using these methods. In some particularly preferred embodiments, the compound(s) identified using the methods of the present invention are provided to an animal to treat neurological illness. In some embodiments, the animal is suffering from a neurological illness. In particularly preferred embodiments, the neurological illness is Alzheimer's disease. In alternative particularly preferred embodiments, the animal is a human.

The present invention also provides methods for identifying compounds that facilitate transport of amyloid precursor protein comprising the steps of: providing an animal capable of producing amyloid precursor protein, wherein the animal has at least one mutation in at least one subunit of kinesin-I, and at least one test compound; administering the test compound(s) to the animal, and detecting the binding of the kinesin-I and amyloid precursor protein. In one embodiment, the test compound inhibits the binding of kinesin-I and amyloid precursor protein, while in an alternative embodiment, the test compound enhances the binding of kinesin-I and amyloid precursor protein. In some embodiments, the kinesin-I encoded by the mutant kinesin-I subunit is functionally normal, while in other embodiments, the kinesin-I encoded by the mutant kinesin-I subunit is mutated. In still further embodiments, the animal having the mutant kinesin-I subunit fails to produce functional kinesin-I. It is not intended that the mutation be limited to any particular mutation, nor is it intended that the mutation particularly affect any specific portion of the kinesin-I molecule. In alternative embodiments, the animal produces abnormal amyloid precursor protein. The present invention further provides compounds identified using these methods.

The present invention also provides methods for treating neurological illness by administering a compound identified using any of the methods described above to an animal suffering from a neurological illness. In some embodiments, the compound administered to the animal inhibits the binding of kinesin-I and amyloid precursor protein, while in alternative embodiments, the compound administered to the animal enhances the binding of kinesin-I and amyloid precursor protein. In particularly preferred embodiments, the compound administered to the animal inhibits or prevents the neuronal transport of amyloid precursor protein. In some preferred embodiments, the neurological illness is Alzheimer's disease. In particularly preferred embodiments, the animal is a human.

Panel E provides results showing that the C-terminus of APP directly binds the TPR domain of KLC1. Purified GST fusion proteins of either the N-terminal coiled-coil domain of KLC1 (GST-CC) or the TPR domains of KLC1 (GST-TPR) or GST alone were incubated with APP-GFP or KIF5B-His or GFP alone and the bound and unbound proteins analyzed using antibodies to the GFP and His tags.

Figure 6A:
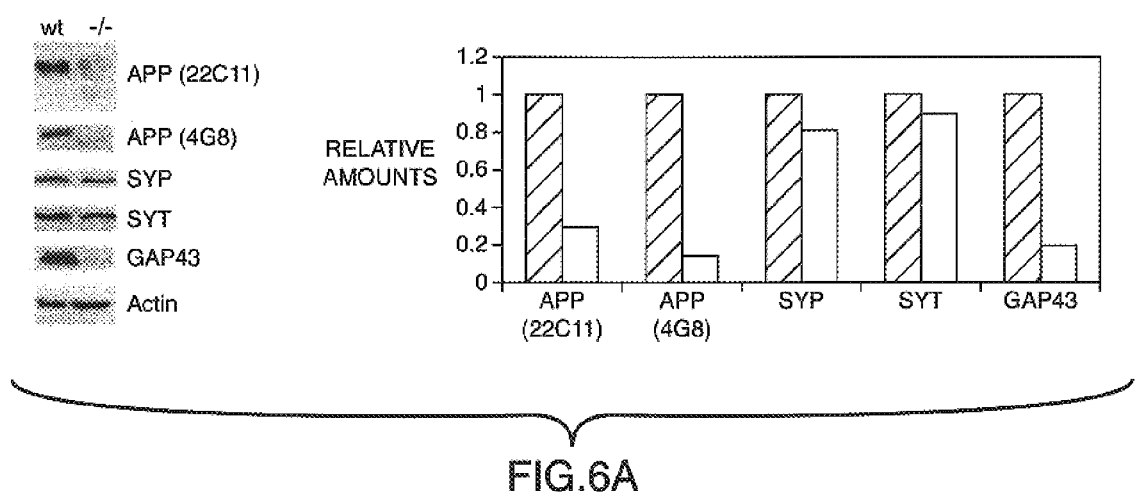
Figure 6B:
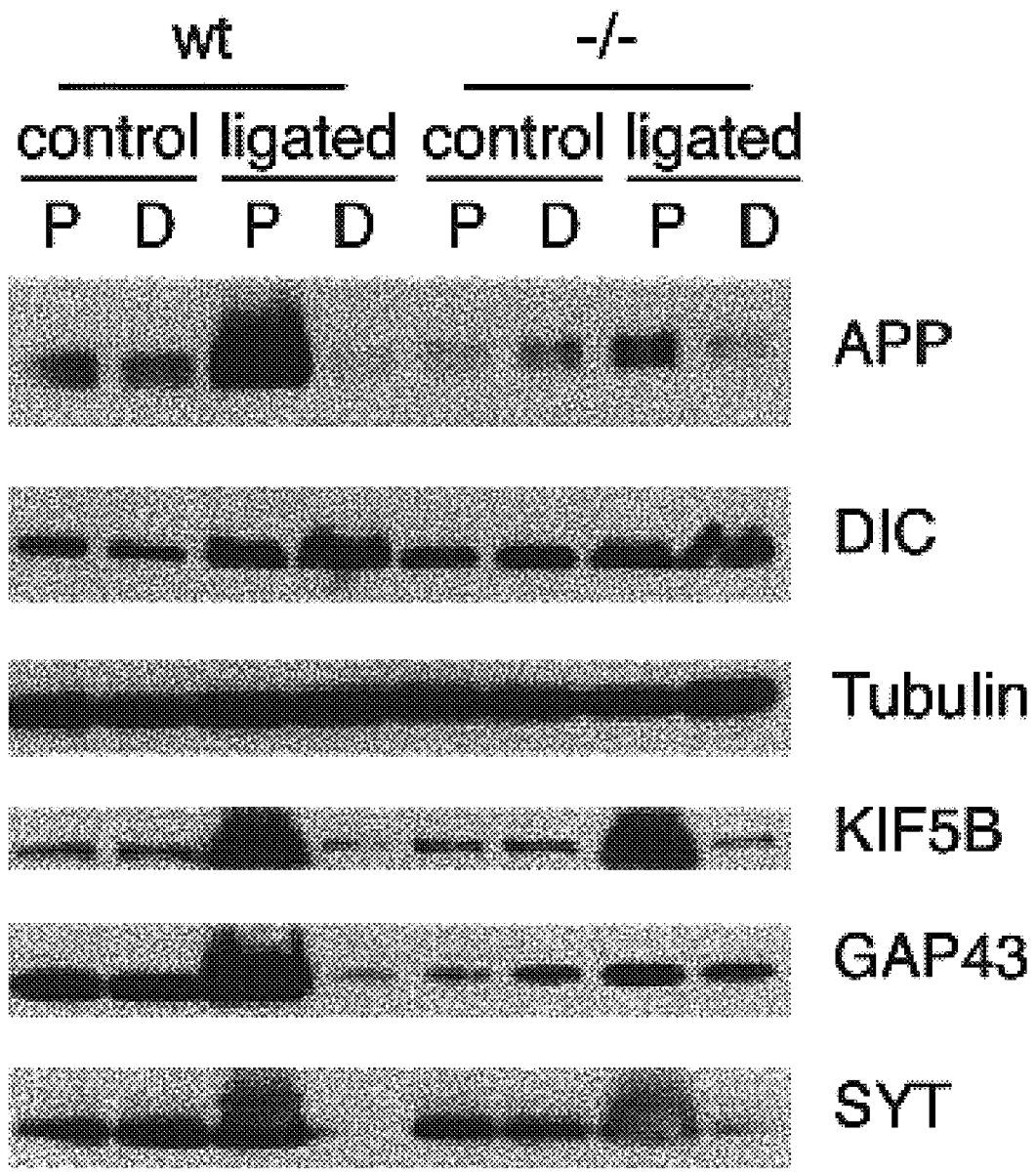

FIGS. 6A–B provides results showing decreased axonal transport of APP in sciatic nerves of KLC1 mutant mice. Panel A provides results for sciatic nerves from wild-type (wt) and mutant (−/−) KLC1 littermate mice that were dissected, homogenized and analyzed by quantitative Western blotting using antibodies to APP (22C11 and 4G8) and non-kinesin-I cargoes, synaptophysin (SYP) and synaptotagmin (SYT). The normalized relative amount of each protein (bar graphs) in wild-type (wt, black bars) was set to 1.0 and the amount of each protein present in the KLC1 mutant (−/−, gray bars) was determined using actin as an internal normalization and loading control. For APP, the lower bands seen on the immunoblot were also included in the quantitation shown in the bar graph. One representative experiment is shown; less than 5% standard deviation in four independent experiments using four different matched pairs of mice was observed. Panel B provides results for sciatic nerves of wild-type (wt) and mutant (−/−) KLC1 mice that were ligated unilaterally at the midpoint. Six hours later the proximal and distal halves of the nerve on either side of the ligature were dissected from the unligated (control) and ligated nerves of each animal. The proximal and distal halves were pooled, homogenized, protein concentration measured, and equal amounts of protein were analyzed by SDS-PAGE and Western blots using antibodies to APP (22C11 shown; 4G8 not shown), dynein intermediate chain (DIC), tubulin, KIF5B, GAP43, and synaptotagmin (SYT).

DEFINITIONS

To facilitate an understanding of the present invention, a number of terms and phrases are defined below:

As used herein, the terms "modulator of transport" refers to a compound, molecule, or composition that is capable of altering the transport of APP. In preferred embodiments, the modulator alters the transport of APP mediated by binding of APP to the kinesin light chain subunit of kinesin-I. This alteration in activity encompasses inhibition (i.e., the compound, molecule or composition is an "inhibitor" of transport), as well as stimulation or enhancement (i.e., the compound, molecule or composition is a "stimulator" or "enhancer" of transport). In some embodiments, these modulators are identified using in vitro and/or in vivo assays, including but not limited to ATPase activity, microtubule gliding, microtubule depolymerizing activity, and binding activity (e.g., microtubule binding activity). In these assays, controls are used in order to permit comparisons between samples.

As used herein, the term "binding of APP and kinesin-I" refers to the interaction of APP and kinesin-I, such that a complex is formed comprising APP and kinesin-I. It is contemplated that such binding be detected by any appropriate means, including but not limited to assay systems such as co-immunoprecipitation methods, co-immunoprecipitation followed by Western blotting, sucrose gradient centrifugation, microtubule binding assays, column chromatography methods, gel overlays, and surface plasmon resonance (e.g., BIAcore).

As used herein, the terms "peptide," "polypeptide" and "protein" all refer to a primary sequence of amino acids that are joined by covalent "peptide linkages." In general, a peptide consists of a few amino acids, typically from 2–50 amino acids, and is shorter than a protein. The term "polypeptide" may encompass either peptides or proteins. A peptide, polypeptide or protein may be synthetic, recombinant or naturally occurring. A synthetic peptide is a peptide which is produced by artificial means in vitro (i.e., was not produced in vivo).

The terms "sample" and "specimen" are used in their broadest sense and encompasses a samples or specimens obtained from any source. As used herein, the term "sample" is used to refer to biological samples obtained from animals (including humans), and encompasses fluids, solids, tissues, and gases. In preferred embodiments of this invention, biological samples include cerebrospinal fluid (CSF), serous fluid, blood, and blood products such as plasma, serum and the like. However, these examples are not to be construed as limiting the types of samples which find use with the present invention.

As used herein, the terms "beta-amyloid protein," "amyloid beta protein," "βA," "βA peptide" and "βA protein" all refer to a protein produced by neurons and glial cells in the brain. βA is found in the brain plaques of patients with Alzheimer's disease, head trauma and Down's syndrome (See e.g., Haass and Selkoe, Cell 75:1039 [1993]; Teller et al., Nature Med., 2:93 [1996]), and is also found normally in the spinal fluid and blood.

As used herein, the term "modified βA peptide" refers to a beta-amyloid peptide that has been oxidatively modified. In one embodiment, the modified βA peptide is oxidatively modified by oxidative stress.

As used herein, the terms "βA-malondialdehyde adduct" or "βA-MDA" refer to an adduct resulting from oxidative stress-induced modifications in the βA peptide. In one embodiment, the βA-malondialdehyde adduct is a malondialdehyde-lysine adduct.

As used herein, the terms "host," "subject" and "patient" refer to any animal, including but not limited to, human and non-human animals (e.g., rodents, arthropods, insects, fish [e.g., zebrafish], non-human primates, ovines, bovines, ruminants, lagomorphs, porcines, caprines, equines, canines, felines, aves, etc.), which is studied, analyzed, tested, diagnosed or treated. As used herein, the terms "host," "subject" and "patient" are used interchangeably.

As used herein, the terms "Alzheimer's disease" or "AD" refer to a neurodegenerative disorder and encompasses familial Alzheimer's disease and sporadic Alzheimer's disease. The term "familial Alzheimer's disease" refers to Alzheimer's disease that is associated with genetic factors, and thus demonstrates inheritance, while "sporadic Alzheimer's disease" refers to Alzheimer's disease that has no prior family history. Symptoms indicative of Alzheimer's disease in a human subject can include, but are not limited to, mild to severe dementia, progressive impairment of memory (ranging from mild forgetfulness to disorientation and severe memory loss), poor visuo-spatial skills, personality changes, poor impulse control, poor judgement, distrust of others, increased stubbornness, restlessness, poor planning ability, poor decision making, and social withdrawal. In severe cases, patients lose the ability to use language and communicate, and require assistance in personal hygiene, eating and dressing, and are eventually bedridden. Hallmark pathologies within brain tissue include extracellular neuritic β-amyloid plaques, neurofibrillary tangles, neurofibrillary degeneration, granulovascular neuronal degeneration, synaptic loss, and extensive neuronal cell death.

As used herein, the term "early-onset Alzheimer's disease" refers to the classification used if Alzheimer's disease is diagnosed to occur before the age of 65 in humans. As used herein, the term "late-onset Alzheimer's disease" refers to the classification used if Alzheimer's disease is diagnosed to occur after the age of 65 in humans.

As used herein, the terms "subject having Alzheimer's disease" or "subject displaying symptoms or pathology indicative of Alzheimer's disease" refers to a subject that is identified as having or likely to have Alzheimer's disease based on known Alzheimer's symptoms and pathology.

As used herein, the term "subject at risk of displaying pathology indicative of Alzheimer's disease" refers to a subject identified as having a risk of developing Alzheimer's disease because of a familial inheritance pattern of Alzheimer's disease in the subject's family.

As used herein, the term "lesion" refers to a wound or injury, or to a pathologic change in a tissue. For example, the amyloid plaque lesions observed in the brains of patients having Alzheimer's disease are considered the hallmark pathology characteristic of the disease.

As used herein, the term "antibody" or "antibodies" refers to any immunoglobulin that binds specifically to an antigenic determinant, and specifically, binds to proteins identical or structurally related to the antigenic determinant which stimulated their production. Thus, antibodies can be used to detect the antigen which stimulated their production. Monoclonal antibodies are derived from a single clone of B lymphocytes (i.e., B cells), and are homogeneous in structure and antigen specificity. Polyclonal antibodies originate from many different clones of antibody-producing cells, and thus are heterogenous in their structure and epitope specificity, but all directed to the same molecule. Monoclonal and polyclonal antibodies may or may not be purified. For example, polyclonal antibodies contained in crude antiserum may be used in this unpurified state. It is intended that the term "antibody" encompass any immunoglobulin (e.g., IgG, IgM, IgA, IgE, IgD, etc.) obtained from any source (e.g., humans, rodents, non-human primates, caprines, bovines, equines, ovines, etc.).

The antibodies used in the methods invention may be prepared using various immunogens. In one embodiment, the immunogen is a kinesin or kinesin subunit (e.g., the kinesin light chain subunit of kinesin I). Such antibodies include, but are not limited to polyclonal, monoclonal, chimeric, single chain, Fab fragments, and an Fab expression library.

Various procedures known in the art may be used for the production of polyclonal antibodies. For the production of antibody, various host animals can be immunized by injection with the peptide corresponding to any molecule of interest in the present invention, including but not limited to rabbits, mice, rats, sheep, goats, etc.

In one preferred embodiment, the peptide is conjugated to an immunogenic carrier (e.g., diphtheria toxoid, bovine serum albumin (BSA), or keyhole limpet hemocyanin [KLH]). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides,oil emulsions, keyhole limpet hemocyanins, dinitrophenol, and potentially useful human adjuvants such as BCG (Bacille Calmette-Guerin) and *Corynebacterium parvum*.

For preparation of monoclonal antibodies directed toward molecules of interest in the present invention, any technique that provides for the production of antibody molecules by continuous cell lines in culture may be used (See, e.g., Harlow and Lane, *Antibodies: A Laboratory Manual*, Cold Spring Harbor Laboratory Press, Cold Spring Harbor, N.Y.). These include but are not limited to the hybridoma technique originally developed by Kohler and Milstein (Köhler and Milstein, Nature 256:495–497 [1975]), as well as the trioma technique, the human B-cell hybridoma technique (See e.g., Kozbor et al. Immunol. Today 4:72 [1983]), and the EBV-hybridoma technique to produce human monoclonal antibodies (Cole et al., in *Monoclonal Antibodies and Cancer Therapy*, Alan R. Liss, Inc., pp. 77–96 [1985]). In some particularly preferred embodiments of the present invention, the present invention provides monoclonal antibodies of the IgG class.

In additional embodiments of the invention, monoclonal antibodies can be produced in germ-free animals utilizing technology such as that described in PCT/US90/02545. In addition, it is contemplated that in some embodiments, human antibodies are used and can be obtained by using human hybridomas (Cote et al., Proc. Natl. Acad. Sci. U.S.A.80:2026–2030 [1983]) or by transforming human B cells with EBV virus in vitro (Cole et al., in *Monoclonal Antibodies and Cancer Therapy*, Alan R. Liss, pp. 77–96 [1985]).

Furthermore, techniques described for the production of single chain antibodies (U.S. Pat. No. 4,946,778; herein incorporated by reference) can be adapted to produce single chain antibodies that specifically recognize a molecule of interest (e.g., the kinesin light chain subunit of kinesin-I, as described herein). An additional embodiment of the invention utilizes the techniques described for the construction of Fab expression libraries (Huse et al., Science 246:1275–1281 [1989]) to allow rapid and easy identification of monoclonal Fab fragments with the desired specificity for a particular kinesin or kinesin epitope of interest (e.g., the kinesin light chain subunit of kinesin-I).

Antibody fragments which contain the idiotype (antigen binding region) of the antibody molecule can be generated by known techniques. For example, such fragments include but are not limited to: the F(ab')2 fragment which can be produced by pepsin digestion of the antibody molecule; the Fab' fragments which can be generated by reducing the disulfide bridges of the F(ab')2 fragment, and the Fab fragments which can be generated by treating the antibody molecule with papain and a reducing agent.

In the production of antibodies, screening for the desired antibody can be accomplished by techniques known in the art (e.g., radioimmunoassay, ELISA [enzyme-linked immunosorbent assay], "sandwich" immunoassays, immunoradiometric assays, gel diffusion precipitin reactions, immunodiffusion assays, in situ immunoassays [using colloidal gold, enzyme or radioisotope labels, for example], Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.

The foregoing antibodies can be used in methods known in the art relating to the localization and structure of molecules involved Alzheimer's disease, including but not limited to kinesins described herein (e.g., for Western blotting to detect the kinesin light chain subunit of kinesin-I), measuring levels thereof in appropriate biological samples, etc. For example, the antibodies can be used to detect proteins of interest in a biological sample from an individual.

The biological samples can then be tested directly for the presence of kinesin moieties (e.g., the kinesin light chain subunit of kinesin-I) of interest using an appropriate immunoassay strategy. Alternatively, proteins in the sample can be size separated (e.g., by polyacrylamide gel electrophoresis (PAGE), in the presence or not of sodium dodecyl sulfate (SDS), and the presence of kinesin(s) of interest is then detected by immunoblotting (Western blotting)).

The foregoing explanations of particular assay systems are presented herein for purposes of illustration only, in fulfillment of the duty to present an enabling disclosure of the invention. It is to be understood that the present invention contemplates a variety of immunochemical assay protocols within its spirit and scope.

The terms "specific binding" or specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labelled "A" and the antibody will reduce the amount of labelled A bound to the antibody.

As used herein, the terms "auto-antibody" or "auto-antibodies" refer to any immunoglobulin that binds specifically to an antigen that is native to the host organism that produced the antibody (i.e., the antigen is not synthetic and/or has not been artificially supplied to the host organism). The presence of auto-antibodies is termed "autoimmunity."

As used herein, the term "antigen" is used in reference to any substance that is capable of reacting with an antibody. It is intended that this term encompass any antigen and "immunogen" (i.e., a substance which induces the formation of antibodies). Thus, in an immunogenic reaction, antibodies are produced in response to the presence of an antigen or portion of an antigen.

The term "antigenic determinant" or "epitope" as used herein refers to that portion of an antigen that makes contact with a particular antibody variable region. When a protein or fragment of a protein is used to immunize a host animal, numerous regions of the protein may induce the production of antibodies which bind specifically to a given region or three-dimensional structure on the protein; these regions or structures are referred to as antigenic determinants.

As used herein, the term "purified" or "to purify" or "purification" refers to the removal or reduction of at least one contaminant from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample (i.e., "enrichment" of an antibody).

The terms "Western blot," "Western immunoblot" "immunoblot" or "Western" refer to the immunological analysis of protein(s), polypeptides or peptides that have been immobilized onto a membrane support. The proteins are first resolved by acrylamide gel electrophoresis to separate the proteins, followed by transfer of the protein from the gel to a solid support, such as nitrocellulose or a nylon membrane. The immobilized proteins are then exposed to an antibody having reactivity towards an antigen of interest. The binding of the antibody (i.e., the primary antibody) is detected by use of a secondary antibody which specifically binds the primary antibody. The secondary antibody is typically conjugated to an enzyme which permits visualization by the production of a colored reaction product or catalyzes a luminescent enzymatic reaction (e.g., the ECL reagent, Amersham).

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., *Molecular Cloning: A Laboratory Manual*, Cold Spring Harbor Press, N.Y., pp 9.31–9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, J. et al., supra, pp 7.39–7.52 [1989]).

As used herein, the term "ELISA" refers to enzyme-linked immunosorbent assay. Numerous methods and applications for carrying out an ELISA are well known in the art, and provided in many sources (See, e.g., Crowther, "Enzyme-Linked Immunosorbent Assay (ELISA)," in *Molecular Biomethods Handbook*, Rapley et al. [eds.], pp. 595–617, Humana Press, Inc., Totowa, N.J. [1998]; Harlow and Lane (eds.), *Antibodies: A Laboratory Manual*, Cold Spring Harbor Laboratory Press [1988]; Ausubel et al. (eds.), *Current Protocols in Molecular Biology*, Ch. 11, John Wiley & Sons, Inc., New York [1994]).

In one embodiment of the present invention, a "direct ELISA" protocol is provided, where an antigen is first bound and immobilized to a microtiter plate well. In an alternative embodiment, a "sandwich ELISA" is provided, where the antigen is attached to the stationary phase by capturing it with an antibody that has been previously bound to the microtiter plate well. The ELISA method detects an immobilized antigen by use of an antibody-enzyme conjugate, where the antibody is specific for the antigen of interest, and the enzyme portion allows visualization and quantitation by the generation of a colored or fluorescent reaction product. The conjugated enzymes commonly used in the ELISA include horseradish peroxidase, urease, alkaline phosphatase, glucoamylase or β-galactosidase. The intensity of color development is proportional to the amount of antigen present in the reaction well.

As used herein, the term "in vitro" refers to an artificial environment and to processes or reactions that occur within an artificial environment. In vitro environments consist of, but are not limited to, controlled laboratory conditions. The term "in vivo" refers to the natural environment (e.g., within an animal or a cell) and to processes or reactions that occur within that natural environment.

As used herein, the term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

"Nucleic acid sequence," "nucleotide sequence" and "polynucleotide sequence" as used herein refer to an oligonucleotide or polynucleotide, and fragments or portions thereof, and to DNA or RNA of genomic or synthetic origin which may be single- or double-stranded, and represent the sense or antisense strand.

As used herein, the terms "oligonucleotides" and "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

The term "nucleotide sequence of interest" refers to any nucleotide sequence, the manipulation of which may be deemed desirable for any reason, by one of ordinary skill in the art. Such nucleotide sequences include, but are not limited to, coding sequences of structural genes (e.g., reporter genes, selection marker genes, oncogenes, drug resistance genes, growth factors, etc.), and of non-coding regulatory sequences that do not encode an mRNA or protein product (e.g., promoter sequence, enhancer sequence, polyadenylation sequence, termination sequence, etc.).

"Amino acid sequence," "polypeptide sequence," "peptide sequence," and "peptide" are used interchangeably herein to refer to a sequence of amino acids.

The term "portion" when used in reference to a nucleotide sequence refers to fragments of that nucleotide sequence. The fragments may range in size from 5 nucleotide residues to the entire nucleotide sequence minus one nucleic acid residue. The term "portion" when used in reference to an amino acid sequence refers to fragments of the amino acid sequence. The fragments may range in size from 3 amino acids to the entire amino acid sequence minus one amino acid residue.

An oligonucleotide sequence which is a "homolog" of a first nucleotide sequence is defined herein as an oligonucleotide sequence which exhibits greater than or equal to 50% identity, and more preferably greater than or equal to 70% identity, to the first nucleotide sequence when sequences having a length of 10 bp or larger are compared.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects that transcription proceeds in a 5' to 3' direction along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

The term "cloning" as used herein, refers to the process of isolating a nucleotide sequence from a nucleotide library, cell or organism for replication by recombinant techniques.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed using a recombinant DNA molecule.

The term "transfection" as used herein refers to the introduction of foreign DNA into cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, biolistics (i.e., particle bombardment) and the like.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "5'-CAGT-3'," is complementary to the sequence "5'-ACTG-3'." Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands may have significant effects on the efficiency and strength of hybridization between nucleic acid strands. This may be of particular importance in amplification reactions, as well as detection methods which depend upon binding between nucleic acids.

The terms "homology" and "homologous" as used herein in reference to nucleotide sequences refer to a degree of complementarity with other nucleotide sequences. There may be partial homology or complete homology (i.e., identity). A nucleotide sequence which is partially complementary (i.e., "substantially homologous") to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

As used herein the term "stringency" is used in reference to the conditions of temperature, ionic strength, and the presence of other compounds such as organic solvents, under which nucleic acid hybridizations are conducted. "Stringency" typically occurs in a range from about $T_m°$ C. to about 20° C. to 25° C. below $T_m$. As will be understood by those of skill in the art, a stringent hybridization can be used to identify or detect identical polynucleotide sequences or to identify or detect similar or related polynucleotide sequences. Under "stringent conditions" the nucleotide sequence portions thereof, will hybridize to its exact complement and closely related sequences.

Low stringency conditions comprise conditions equivalent to binding or hybridization at 68° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5×Denhardt's reagent (50×Denhardt's contains per 500 ml: 5 g Ficoll (Type 400, Pharmacia), 5 g BSA (Fraction V; Sigma)) and 100 µg/ml denatured salmon sperm DNA followed by washing in a solution comprising 2.0×SSPE, 0.1% SDS at room temperature when a probe of about 100 to about 1000 nucleotides in length is employed.

It is well known in the art that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol), as well as components of the hybridization solution may be varied to generate conditions of low stringency hybridization different from, but equivalent to, the above listed conditions. In addition, conditions which promote hybridization under conditions of high stringency (e.g., increasing the temperature of the hybridization and/or wash steps, the use of formamide in the hybridization solution, etc.) are well known in the art. High stringency conditions, when used in reference to nucleic acid hybridization, comprise conditions equivalent to binding or hybridization at 68° C. in a solution consisting of 5×SSPE, 1% SDS, 5×Denhardt's reagent and 100 µg/ml denatured salmon sperm DNA followed by washing in a solution comprising 0.1×SSPE and 0.1% SDS at 68° C. when a probe of about 100 to about 1000 nucleotides in length is employed.

When used in reference to a double-stranded nucleic acid sequence such as a cDNA or genomic clone, the term "substantially homologous" refers to any probe which can hybridize either partially or completely to either or both strands of the double-stranded nucleic acid sequence under conditions of low stringency as described above.

When used in reference to a single-stranded nucleic acid sequence, the term "substantially homologous" refers to any probe which can hybridize (i.e., it is the complement of) the single-stranded nucleic acid sequence under conditions of low stringency as described above.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an anti-parallel configuration. A hybridization complex may be formed in solution (e.g., $C_0t$ or $R_0t$ analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G}+\text{C})$, when a nucleic acid is in aqueous solution at 1 M NaCl (see e.g., Anderson and Young, Quantitative Filter Hybridization, in *Nucleic Acid Hybridization* [1985]). Other references include more sophisticated computations which take structural as well as sequence characteristics into account for the calculation of $T_m$.

The term "heterologous nucleic acid sequence" or "heterologous DNA" are used interchangeably to refer to a nucleotide sequence which is ligated to a nucleic acid sequence to which it is not ligated in nature, or to which it is ligated at a different location in nature. Heterologous DNA is not endogenous to the cell into which it is introduced, but has been obtained from another cell. Generally, although not necessarily, such heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), etc. "Amplification" is defined herein as the production of additional copies of a nucleic acid sequence and is generally carried out using polymerase chain reaction technologies well known in the art (see, e.g., Dieffenbach and Dveksler, *PCR Primer, a Laboratory Manual*, Cold Spring Harbor Press, Plainview N.Y. [1995]). As used herein, the term "polymerase chain reaction" ("PCR") refers to the methods of U.S. Pat. Nos. 4,683,195, 4,683,202, and 4,965,188, all of which are hereby incorporated by reference, which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

The terms "reverse transcription polymerase chain reaction" and "RT-PCR" refer to a method for reverse transcription of an RNA sequence to generate a mixture of cDNA sequences, followed by increasing the concentration of a desired segment of the transcribed cDNA sequences in the mixture without cloning or purification. Typically, RNA is reverse transcribed using a single primer (e.g., an oligo-dT primer) prior to PCR amplification of the desired segment of the transcribed DNA using two primers.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and of an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that it is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the terms "restriction endonucleases" and "restriction enzymes" refer to bacterial enzymes, each of which cut double- or single-stranded DNA at or near a specific nucleotide sequence.

As used herein, the term "an oligonucleotide having a nucleotide sequence encoding a gene" means a nucleic acid sequence comprising the coding region of a gene, i.e. the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements (e.g., enhancers, promoters, splice junctions, polyadenylation signals, etc.) may be placed in close proximity to the coding region of the gene if needed to permit proper initiation of transcription and/or correct processing of the primary RNA transcript. Alternatively, the coding region utilized in the expression vectors of the present invention may contain endogenous enhancers, splice junctions, intervening sequences, polyadenylation signals, or a combination of both endogenous and exogenous control elements.

Transcriptional control signals in eukaryotes comprise "enhancer" elements. Enhancers consist of short arrays of DNA sequences that interact specifically with cellular proteins involved in transcription (Maniatis et al., Science 236:1237 [1987]). Enhancer elements have been isolated from a variety of eukaryotic sources including genes in plant, yeast, insect and mammalian cells and viruses. The selection of a particular enhancer depends on what cell type is to be used to express the protein of interest.

The presence of "splicing signals" on an expression vector often results in higher levels of expression of the recombinant transcript. Splicing signals mediate the removal of introns from the primary RNA transcript and consist of a splice donor and acceptor site (Sambrook, et al., *Molecular Cloning: A Laboratory Manual*, 2nd ed., Cold Spring Harbor Laboratory Press, New York, pp. 16.7–16.8 [1989]). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is isolated from one gene and placed 3' of another gene.

The term "promoter," "promoter element," or "promoter sequence" as used herein, refers to a DNA sequence which when placed at the 5' end of (i.e., precedes) an oligonucleotide sequence is capable of controlling the transcription of the oligonucleotide sequence into mRNA. A promoter is typically located 5' (i.e., upstream) of an oligonucleotide sequence whose transcription into mRNA it controls, and provides a site for specific binding by RNA polymerase and for initiation of transcription.

The term "promoter activity" when made in reference to a nucleic acid sequence refers to the ability of the nucleic acid sequence to initiate transcription of an oligonucleotide sequence into mRNA.

As used herein, the terms "nucleic acid molecule encoding," "nucleotide encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "isolated" when used in relation to a nucleic acid, as in "an isolated oligonucleotide" refers to a nucleic acid sequence that is separated from at least one contaminant nucleic acid with which it is ordinarily associated in its natural source. Isolated nucleic acid is nucleic acid present in a form or setting that is different from that in which it is found in nature. In contrast, non-isolated nucleic acids are nucleic acids such as DNA and RNA which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs which encode a multitude of proteins. However, isolated nucleic acid encoding a polypeptide of interest includes, by way of example, such nucleic acid in cells ordinarily expressing the polypeptide of interest where the nucleic acid is in a chromosomal or extrachromosomal location different from that of natural cells, or is otherwise flanked by a different nucleic acid sequence than that found in nature. The isolated nucleic acid or oligonucleotide may be present in single-stranded or doublestranded form. Isolated nucleic acid can be readily identified (if desired) by a variety of techniques (e.g., hybridization, dot blotting, etc.). When an isolated nucleic acid or oligonucleotide is to be utilized to express a protein, the oligonucleotide will contain at a minimum the sense or coding strand (i.e., the oligonucleotide may be singlestranded). Alternatively, it may contain both the sense and anti-sense strands (i.e., the oligonucleotide may be double-stranded).

As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

As used herein, the term "structural gene" or "structural nucleotide sequence" refers to a DNA sequence coding for RNA or a protein which does not control the expression of other genes. In contrast, a "regulatory gene" or "regulatory sequence" is a structural gene which encodes products (e.g., transcription factors) which control the expression of other genes.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements include splicing signals, polyadenylation signals, termination signals, etc.

As used herein, the term "gene" means the deoxyribonucleotide sequences comprising the coding region of a structural gene. A "gene" may also include non-translated sequences located adjacent to the coding region on both the 5' and 3' ends such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogenous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

A "non-human animal" refers to any animal which is not a human and includes vertebrates such as rodents, non-human primates, ovines, bovines, ruminants, lagomorphs, porcines, caprines, equines, canines, felines, aves, etc. Preferred nonhuman animals are selected from the order Rodentia.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro.

A "transformed cell" is a cell or cell line that has acquired the ability to grow in cell culture for many multiple generations, the ability to grow in soft agar and the ability to not have cell growth inhibited by cell-to-cell contact. In this regard, transformation refers to the introduction of foreign genetic material into a cell or organism. Transformation may be accomplished by any method known which permits the successful introduction of nucleic acids into cells and which results in the expression of the introduced nucleic acid. "Transformation" includes but is not limited to such methods as transfection, microinjection, electroporation, and lipofection (liposome-mediated gene transfer). Transformation may be accomplished through use of any expression vector. For example, the use of baculovirus to introduce foreign nucleic acid into insect cells is contemplated. The term "transformation" also includes methods such as P-element mediated germline transformation of whole insects. Additionally, transformation refers to cells that have been transformed naturally, usually through genetic mutation.

As used herein, the term "kit" is used in reference to a combination of reagents and other materials. It is contemplated that the kit may include reagents such as antibodies, control proteins, as well as testing containers (e.g., microtiter plates, etc.). It is not intended that the term "kit" be limited to a particular combination of reagents and/or other materials.

DESCRIPTION OF THE INVENTION

The present invention provides methods and compositions for the treatment of Alzheimer's disease. In particular, the present invention provides methods and compositions suitable to assess inhibitors of neuronal transport of Alzheimer's amyloid precursor protein.

As indicated above, Alzheimer's disease (AD) is a progressive, neurodegenerative disorder characterized by extracellular deposition of amyloid protein. The amyloid deposits are mainly composed of an insoluble peptide, the amyloid beta peptide (Aβ), which is derived from proteolytic cleavage of the amyloid precursor protein (APP). Numerous studies have suggested that aberrant trafficking or processing of APP may play a causative role in AD (reviewed in Selkoe, Nature 39 (Suppl) A23–30 [1999]; Sinha and Lieberburg, Proc. Natl. Acad. Sci. USA 96:11049–11053 [1999]; and De Strooper and Annaert, J. Cell. Sci., 113:1857–1870 [2000]). Thus, methods and compositions to elucidate the normal mechanisms of axonal transport and trafficking of APP are essential to elucidating how APP participates in the development of AD and in the identification and characterization of treatment regimens to alleviate the signs and symptoms of Alzheimer's disease.

In neurons, APP is transported within axons by fast anterograde axonal transport from the neuronal cell bodies to the distal nerve terminals (Koo et al., Proc. Natl. Acad. Sci. USA 87:1561–1565 [1990]; and Sisodia et al., J. Neurosci., 13:3136–3142 [1993]). Anti-sense inhibition experiments using oligonucleotides complementary to kinesin heavy chain coding sequences in hippocampal neurons suggested that axonal transport of APP requires the microtubule-dependent motor protein kinesin-I (Amaratunga et al., J. Neurochem., 64:2374–2376 [1995]; Ferreira et al., J. Neurosci., 12:3112–3123 [1993]; Kaether et al., Mol. Biol. Cell 11:1213–1224 [2000]; and Yamazaki et al., J. Cell. Biol., 129:431–442 [1995]). However, a prominent gap is the lack of information about whether, or how APP interacts with components of the neuronal kinesin-I transport machinery.

Kinesin-I

Kinesin-I was the first member of the kinesin superfamily to be identified (Brady, Nature 317:73–75 [1985]; and Vale et al., Cell 42:39–50 [1985]), and is responsible for ATP-dependent movement of vesicular cargoes within cells (reviewed in Goldstein and Philip, Ann. Rev. Cell Dev. Biol., 15:141–183 [1999]; Goldstein and Yang, Ann. Rev. Neurosci., 23:39–72 [2000]; and Kamal and Goldstein, Curr. Opin. Cell Biol., 12:503–508 [2000]). Kinesin-I is composed of two kinesin heavy chain (KHC) and two kinesin light chain (KLC) subunits. In the mouse, there are three genes encoding KHC (KIF5A, KIF5B, and KIF5C) and three genes encoding KLC (KLC1, KLC2, and KLC3) (See e.g., Rahman et al., J. Cell. Biol., 146:1277–1288 [1998]; and Xia et al., Genomics 52:209–213 [1998]). These KHC and KLC subunits appear to associate in all possible combinations (Rahman et al., [1998], supra; Xia et al., [1998], supra). KIF5A and KIF5C are neuron specific isoforms, whereas KLC1 is neuronally enriched. KIF5B and KLC2 are ubiquitously expressed; the expression pattern of KLC3 is unknown.

Both KHC and KLC have distinct conserved domains. KHC has an N-terminal motor domain (Yang et al., Cell 56:879–889 [1989]), a central alpha-helical coiled-coil stalk domain (de Cuevas et al., J. Cell Biol., 116:957–965 [1992]; Gauger and Goldstein, J. Biol. Chem., 268:13657–13666 [1990]; and Hirokawa et al., Cell 56:867–878 [1989]), and a globular C-terminal tail domain, perhaps involved in cargo-binding (Bi et al., J. Cell. Biol., 138:999–1008 [1997]; Seiler et al., Nat. Cell Biol., 2:333–338 [2000]; and Skoufias et al., J. Biol. Chem., 269:1477–1485 [1994]) or motor regulation (Coy et al., Nat. Cell Biol., 1:288–292 [1999]; Friedman and Vale, Nat. Cell Biol., 1:293–297 [1999]; Hackney and Stock, Nature Cell Biol., 2:257–260 [2000]; and Stock et al., J. Biol. Chem., 274:14617–14623 [1999]). KLC has a conserved N-terminal coiled-coil domain that binds KHC (Diefenbach et al., Biochem., 37:16663–16670 [1998]; and Gauger and Goldstein, [1993], supra), and a C-terminal domain that consists of six imperfect repeats of a 34 amino acid tetra-trico peptide repeat (TPR) module (Gindhart and Goldstein, Trends Biochem. Sci., 21:52–53 [1996]). Although the function of the TPR domain in KLC is unknown, TPR domains are involved in protein-protein interactions in a large group of structurally and functionally diverse proteins (Lamb et al., Trends Biochem. Sci., 20:257–259 [1995]; and Blatch and Lassie, Bioessays 21:932–939 [1999]), and could thus be involved in linking KLC to receptor proteins in vesicular or organellar cargoes. Whether KLC interacts directly with membrane associated receptor proteins in vesicles, and what the identity of such motor-binding receptor proteins might be is unknown.

Previously, a candidate kinesin-I receptor protein called kinectin (Kumar et al., Science 267:1834–1837 [1995]; and Toyoshima et al., J. Cell Biol., 118:1121–1131 [1992]) was described and found to be largely absent from axons (Toyoshima and Sheetz, Neurosci. Lett., 211:171–174 [1996]). Thus, kinectin cannot support transport of APP and other proteins used at nerve termini. Some recent experiments have suggested that "cargo" molecules themselves might interact directly with microtubule-dependent motor proteins (See e.g., Tai et al., Cell 97:877–887 [1999]). However, until the development of the present invention, the association of APP with the KLC subunit of kinesin-I was unknown. The data obtained during the development of the present invention indicate that APP transport from sites of synthesis in the neuronal cell body to sites of utilization or pathogenesis at the axonal terminus, as well as within the axon, is mediated by direct binding of APP to KLC.

Kinesin-I and APP Complexes

As indicated herein, results obtained during the development of the present invention indicate that axonal transport of APP requires the formation of a complex containing kinesin-I and APP by direct binding of APP to the KLC subunit of kinesin-I. This conclusion is supported by several lines of evidence, including co-immunoprecipitation, sucrose gradients, and direct in vitro binding experiments, as described herein. In addition, association of APP with microtubules and axonal transport of APP was found to be greatly diminished in a mouse mutant of KLC1, thus providing compelling evidence for the role of KLC in the microtubule based axonal transport of APP in neurons. Thus, the results obtained during the development of the present invention provides direct molecular evidence about the mechanism of axonal transport of APP, and identifies APP as a likely membrane cargo receptor for kinesin-I. However, an understanding of the mechanism(s) is not necessary in order to use the present invention and it is not intended that the present invention be limited to any particular mechanism(s).

The Role of Kinesin-I in Axonal Transport of APP

The results described herein confirm and extend earlier suggestions that kinesin-I might drive the fast anterograde axonal transport of APP. These early suggestions were based on antisense experiments that found decreased APP transport when the expression of the KHC subunit of kinesin-I was inhibited in rabbit optic nerve or hippocampal neurons (Amaratunga et al., J. Neurochem., 64:2374–2376 [1995]; Ferreira et al., J. Neurosci., 13:3112–3123 [1993]; Kaether et al., Mol. Biol. Cell 11:1213–1224 [2000]; and Yamazaki et al., J. Cell. Biol., 129:431–442 [1995]). However, these earlier studies are difficult to interpret since simultaneous inhibition of the transport of the non-kinesin-I cargo, synaptophysin (Okada et al., Cell 81:769–780 [1995]), was also observed (Amaratunga et al., [1995], supra). Thus, work described herein that shows a direct biochemical interaction between APP and KLC, and the dramatic reduction of axonal transport of APP in a gene-targeted mouse mutant of KLC is the most direct in vivo evidence for the role of kinesin-I in the transport of APP.

Recently, yeast two-hybrid analyses identified a protein (PAT1) that binds to the C-terminal basolateral-sorting signal of APP and was suggested to play a role in the transport of APP (Zheng et al., Proc. Natl. Acad. Sci. USA 95:14745–14750 [1998]). Interestingly, PAT1 expressed in transfected cells co-sediments with microtubules, and also possesses TPR repeat domains similar to those found in KLC and other TPR-containing proteins. However, the TPR domains of PAT1 are only 26% identical to the TPR domains of KLCs, and the overall sequence of PAT1 is only 15% identical to KLC. In addition, although PAT1 is reported to associate with a 110 KDa protein, this protein is clearly not KHC (Zheng et al., [1998], supra). Thus it appears that PAT1 is not a true homolog of KLC, but instead may be a microtubule interacting protein that also binds APP. It is possible that PAT1 has a function at the nerve terminus after APP is delivered there by kinesin-I, although whether PAT1 is expressed in neurons is unknown. Indeed, an understanding of the mechanism(s) involved is not necessary in order to use the present invention.

It is intriguing that overexpression of an APP homologue (APPL) in Drosophila neurons leads to axonal blockage and neuronal dysfunction that is synergistic with overexpression of the microtubule-associated protein tau (See, Torroja et al., Curr. Biol., 9:489–492 [1999]). This axonal blockage phenotype is similar to what is observed in Drosophila mutants lacking known kinesin (See, Gindhart et al., J. Cell Biol., 141:443–452 [1998]; Hurd and Saxton, Genetics 144:1075–1085 [1996]; and Hurd et al., Genetics 142:195–204 [1996]) and dynein (Bowman et al., J. Cell. Biol., 146:165–179 [1999]; and Martin et al., Mol. Cell Biol., 10:3717–3728 [1999]) motor subunits or other membrane proteins that bind kinesin-I (Bowman et al., [2000], supra). Besides the phenotypic similarity between APPL overexpression and mutations in microtubule motor subunits, a genetic interaction between APPL and the KHC gene was also demonstrated (Torroja et al., [1999], supra), further supporting a direct functional association of APP and kinesin-I.

Potential Role of APP as a Membrane Cargo Receptor for Kinesin-I

One of the most poorly understood aspects of microtubule-dependent trafficking is the identity of the membranous cargo that each motor carries. Although an understanding of the mechanism(s) is not necessary in order to use the present invention, it is thought that motor-cargo recognition may require three players: the motor proteins, a cargo-bound receptor and accessory components. The results obtained during the development of the present invention indicate that APP may be a membrane cargo receptor for kinesin-I and might link kinesin-I to a particular subset of axonal transport vesicles. This hypothesis is consistent with the finding that APP, a kinesin-I cargo, is enriched in Rab5-positive vesicles whereas there is virtually no APP present in synaptophysin positive vesicles that are most likely cargoes for the UNC104/KIF1A kinesin (See, Ikin et al., J. Biol. Chem., 271:31783–31786 [1996]; Okada et al., Cell 81:769–780 [1995]; Otsuka et al., Neuron 6:113–122 [1991]; and Yonekawa et al., J. Cell Biol., 141:431–441 [1998]). These data indicate that different motors could interact with different membrane cargo receptors on particular subsets of axonal transport vesicles. However, an understanding of the mechanism(s) is not necessary in order to use the present invention.

As indicated above, one previously reported potential receptor for kinesin-I was kinectin, an integral membrane protein that is localized to the endoplasmic reticulum (Kumar et al., Science 267:1834–1837 [1995]; and Toyoshima et al., J. Cell Biol., 118:1121–1131 [1992]). However, proteins other than kinectin might be important for axonal transport since kinectin has been reported to be absent from axons (Toyoshima and Sheetz, Neurosci. Lett., 211:171–174 [1996]). In addition, no direct connection between kinectin and either subunit of kinesin-I has been demonstrated, and kinectin is not found in C. elegans or Drosophila (Rubin et al., Science 287:2204–2215 [2000]).

Recently, analysis of an axonal transport mutant in Drosophila led to the identification of a novel membrane associated protein, Sunday-driver (SYD), which may also be a membrane receptor for kinesin-I (Bowman et al., [2000], supra). GFP-tagged mammalian SYD localized to tubular and vesicular elements that co-stained with kinesin-I and Golgi markers, suggesting that SYD might function as a membrane associated receptor for the axonal transport of post-Golgi vesicles. Thus, it is contemplated that both APP and SYD could be membrane cargo receptors for kinesin-I in axonal transport and post-Golgi transport. However, an understanding of the mechanism(s) involved is not necessary in order to use the present invention.

The Role of KLC in the Interaction of Kinesin-I With Cargo

Results obtained during the development of the present invention indicate that KLC interacts with membrane associated proteins through one or more of its TPR repeat domains. The binding stoichiometry observed of two APP molecules per KLC fits well with the atomic structure of other TPR domains, which indicates that three TPR repeats fold together to bind one ligand (Blatch and Lassie, Bioessays 21:932–939 [1999]; and Scheufler et al., Cell 101:199–210 [2000]). The KLC construct used during the development of the present invention has six TPR repeats so the observed binding stoichiometry fits the theoretical binding saturation that is predicted from the atomic structure. It is intriguing that the observation that APP directly binds to the TPR domain of KLC and that APP binding to KLC is inhibited by the KLC-A11 antibody, which binds specifically to the TPR domain of KLC (Stenoien and Brady, [1997], supra), is similar to recent work on the SYD protein. The SYD protein directly interacts with the TPR domain of KLC by yeast two-hybrid analyses and the KLC-A11 antibody also inhibits binding of SYD to KLC in GST pulldown experiments (Bowman et al., [2000], supra). Strikingly, in an in vitro organelle motility system, the KLC-A11 antibody inhibits the binding of kinesin-I to membranes and blocks fast axonal transport, while no such effects were seen with the 63–90 antibody, which recognizes the N-terminal domain of KLC (Stenoien and Brady, [1997], supra).

Together, these results demonstrate that the TPR domains of KLC directly interact with membrane-associated proteins of vesicular cargo.

Although taken in isolation, the data discussed herein are most consistent with the simple suggestion that the function of the KLC subunit of kinesin-I is to directly bind cargo receptor proteins such as APP, previous studies of the relative roles of KLC and KHC in cargo-attachment and motor regulation have yielded apparently contradictory results. For example, while antibody inhibition studies suggest that KLC is needed for interaction of kinesin-I with membranes (Stenoien and Brady, [1997], supra), another study showed that KHC alone is sufficient to bind membranes (Skoufias et al., J. Biol. Chem., 269:1477–1485 [1994]). This latter finding is consistent with recent work on a null mouse mutant of KLC1 that found KHC accumulation in the absence of KLC at the Golgi apparatus, a presumed site of cargo transport initiation (Rahman et al., [1999], supra). This apparent binding of KHC to potential cargoes in vivo, in the absence of KLC, is also consistent with work on fungal kinesin-I, which has no KLC subunit, yet appears to be capable of cargobinding (Steinberg and Schwila, Mol. Cell Biol., 6:1605–1618 [1995]). There has also been conflicting evidence about whether KLC, or the tail of KHC, or both repress kinesin-I motor activity in the absence of membrane or cargo binding (See, Coy et al., Nat. Cell Biol., 1:288–292 [1999]; Friedman and Vale, Nat. Cell Biol., 1:293–297 [1999]; Stock et al., [1999], supra; and Verhey et al., J. Cell Biol., 143:1053–1066 [1998]). The inconsistencies among these studies could be attributable to the various experimental systems used. However, based upon the results obtained during the development of the present invention, it is contemplated that both KLC and the tail of KHC combine to fully repress motor activity, that the tail of KHC binds relatively indiscriminately to membrane cargoes, and that KLC interaction with specific membrane proteins (such as APP or SYD) relieves motor repression and activates transport. Thus, it is contemplated that the role of KLC is to provide specificity for cargo binding and transport, perhaps via an activation function. However, an understanding of the mechanism(s) is not necessary in order to use the present invention.

Significance of APP Interaction With Kinesin-I in Alzheimer's Disease

There are numerous suggestions that aberrant trafficking or transport of APP may contribute to the development of AD (reviewed in Checler, J. Neurochem., 65:1431–1444 [1995]; Selkoe, Nature 39 Suppl.:A23–A30 [1998]; and Sinha and Lieberburg, Proc. Natl. Acad. Sci. USA 96:11049–11053 [1999]). The finding of a direct interaction of APP and the microtubule transport machinery described herein, leads to the intriguing indication that abnormal interactions of APP and kinesin-I play a role in the pathogenesis of AD, perhaps by blocking or otherwise interfering with normal axonal transport. However, an understanding of the mechanism(s) is not necessary in order to use the present invention.

Indeed, the methods and compositions of the present invention provide means to identify compounds that are effective in alleviating the signs and symptoms of Alzheimer's disease. In particular, the present invention provides assay systems to detect normal APP or C-terminal fragments of APP. In some embodiments, these assays are conducted in solution, while in other embodiments, these assays involve solid-phase binding. In still further embodiments, the present invention provides competition assays. In some embodiments, complete APP is used, while in other embodiments, proteolytic fragments or recombinantly produced fragments of APP are utilized.

Assay Systems for Detection of APP Stimulation of ATPase of Kinesin-I

As indicated above, the present invention further provides assay systems for the detection of APP stimulation of the ATPase of kinesin-I. In some embodiments, the assay involves direct stimulation of kinesin-I (i.e., in solution), while in other embodiments, native kinesin-I is captured from solution and the ATPase reaction is observed. In preferred embodiments, APP binding to kinesin-I is assayed based on its ability to bind ATPase or stimulate ATPase activity. In still further embodiments, the presence or absence of APP or kinesin-I in a sample is detected. In additional embodiments, in situ immunocytochemistry methods are used to detect the binding of APP and kinesin-I in tissues and/or organ samples. In particularly preferred embodiments, the antibodies and other reagents described herein are utilized in these assay systems.

In some binding assays, the ability of a test agent or compound to specifically bind to APP and/or kinesin-I alone, or in a complex is determined. In a particularly preferred embodiment, the ability of a test compound to bind to the light chain of kinesin-I is assessed. There are a wide variety of formats available for appropriate binding assays. In one embodiment, APP or kinesin-I is immobilized on a surface and exposed to the test compound, while in other embodiments, test compounds are immobilized on a surface and the specific binding of APP and/or kinesin-I is assayed. Binding is often easier to detect in systems in which the test compound, APP, and/or kinesin-I are labeled (e.g., with fluorescence, radioactivity, an enzyme, etc., as known in the art). After exposing the components to each other and washing off unbound reagents, the presence of the labeled moiety (i.e., bound to the unlabelled component of the test system).

Solution phase binding assays are also known to those in the art. For example, in one embodiment, the binding assay is a cosedimentation assay. In this assay system, when the test compound binds to APP and/or kinesin-I, the bound test compound and APP and/or kinesin-I cosediment when centrifuged. Unbound APP and/or kinesin-I and test compound either sediment at a different rate or remain in solution.

Methods for performing various binding assays are known in the art, including but not limited to the assay systems such as those described in U.S. patent application Ser. No. 60/057,895 and related PCT application US98/18368. Various references provide general descriptions of various formats for protein binding assays, including competitive binding assays and direct binding assays, (See e.g., Stites and Terr, *Basic and Clinical Immunology*, 7 th ed. [1991]; Maggio, *Enzyme Immunoassay* CRC Press, Boca Raton, Fla. (1980); and Tijssen, *Practice and Theory of Enzyme Immunoassays*, in *Laboratory Techniques in Biochemistry and Molecular Biology*, Elsevier Science Publishers, B. V. Amsterdam, [1985]). In some particularly preferred embodiments, high-throughput assays are contemplated for use in the present invention to identify compounds that inhibit or enhance binding of APP and kinesin-I. It is not intended that the present invention be limited to any particular high-throughput method, as it is contemplated that various methods will find use in the present invention.

Solid-Phase Assay Systems

Thus, in some embodiments, immunoassays are provided in which APP is bound to a solid support (e.g., the well of a microtiter plate, a microcard, or any other suitable format), a sample suspected of containing kinesin-I, and observing the binding of the kinesin-I to the bound APP (i.e., present in a complex of APP and kinesin-I). Thus, in these embodiments, one or more of the assay components are attached to a solid surface. In some embodiments, an ATPase assay system is then used (as known in the art) to detect the stimulation of ATPase activity due to the binding of APP to kinesin-I. In alternative embodiments, an indirect immunoassay system is used in which the complex is detected by the addition of antibodies directed against kinesin-I to the test mixture, as known in the art.

Virtually any solid surface is suitable, as long as the surface material is compatible with the assay reagents and it is possible to attach the component to the surface without unduly altering the reactivity of the assay components. Those of skill in the art recognize that some components exhibit reduced activity in solid phase assays, but this is generally acceptable, as long as the activity is sufficient to be detected and/or quantified.

Solid supports include, but are not limited to any solid surface (e.g., glass beads, planar glasses, controlled pore glasses, plastic porous plastic metals, or resins to which the molecule may be adhered, etc.). Those of skill in the art recognize that in some embodiments, the solid supports of the present invention are derivatized with functional groups (e.g., hydroxyls, amines, carboxyls, esters, and sulfhydryls) to provide reactive sites for the attachment of linkers or the direct attachment of the test compound or other assay component.

Adhesion of the assay component (e.g., APP or kinesin-I) to the solid support can be direct (i.e., the component directly contacts the solid surface) or indirect (i.e., a particular compound or compounds [e.g., APP or kinesin-I] is/are bound to the support, and the other assay component (e.g., kinesin-1 or APP) binds to this compound or compounds rather than to the solid support). In some embodiments, the compound is covalently immobilized (e.g., utilizing single reactive thiol groups of cysteine for anchoring protein components [See e.g., Colliuod et al., Bioconjug. Chem., 4:528–536 (1993)], or non-covalently, but specifically (e.g., via immobilized antibodies or other specific binding proteins [See e.g., Schuhmann, Adv. Mater., 3:388–391 (1991); Lu et al., Anal. Chem., 67:83–87 (1995)]), the biotin/streptavidin system (See e.g., Iwane et al., Biophys. Biochem. Res. Commun., 230:76–80 [1997]), or metal-chelating Langmuir-Blodgett films (See e.g., Ng et al., Langmuir 11:4048–4055 [1995]; Schmitt et al., Angew. Chem. Int. Ed. Engl., 35:317–320 [1996]; Frey et al., Proc. Natl. Acad. Sci. USA 93:4937–4941 [1996]; and Kubalek et al., J. Struct. Biol., 113:117–123 [1994]), and metal-chelating self-assembled monolayers (See e.g., Sigal et al., Anal. Chem., 68:490–497 [1996]), for binding of polyhistidine fusion proteins.

In some embodiments, standard direct or indirect ELISA, IFA, or RIA methods as known in the art are used to detect the binding of APP or kinesin-I. In some embodiments, APP is detected in a sample, while in other embodiments, kinesin-I is detected. Thus, it is clear that the methods of the present invention are adaptable to the detection, identification, and characterization of multiple elements (e.g., APP, kinesin-I, the light chain of kinesin-I, fragments of either APP or kinesin-I, etc.).

Thus, in some embodiments of the methods of the present invention, a sandwich ELISA (enzyme-linked immunosorbent assay) with a monoclonal or polyclonal antibody for capture (i.e., a capture antibody) and a secondary antibody (i.e., a reporter antibody) for detection of bound monoclonal antibody-antigen complex (i.e., APP bound to anti-APP antibody or kinesin-I bound to anti-kinesin-I antibody) is used. In some embodiments, measures are included in order to reduce background noise, as discussed below.

In some ELISA embodiments, alkaline phosphatase conjugates are used, while in other embodiments, horseradish peroxidase conjugates are used. In addition, avidin-biotin systems are contemplated, for assay systems in which increased signal is desired. Thus, in one method of the present invention, 100 $\mu$l biotinylated antibody (e.g., directed against either APP or kinesin-I) appropriately diluted in blocking buffer is added to each well of avidin-precoated ELISA plates (e.g., the neutravidin plates commercially available from Pierce). After 2 hr, the plate is washed with wash buffer (e.g., TBS/Tween 20 0.1%, with or without a blocking agent). Further nonspecific binding is inhibited by adding blocking buffer (e.g., by adding 300 $\mu$l SuperBlock (Pierce) twice, as per the manufacturer's recommendations). Following incubation to allow binding of the biotinylated antibody to the surfaces of the wells, the plate is washed (e.g., 3 times) as known in the art, to remove any unbound antibody present in the wells.

Samples suspected of containing either APP or kinesin-I are diluted with an appropriate buffer and added to the wells of the ELISA plate, as well as standards and controls. The diluted standards, controls, and samples, are added to the wells of the ELISA plate) (e.g., 100 hundred $\mu$l/well). Standards, controls, and samples are tested in duplicate. The plate is incubated overnight or for another appropriate length of time, typically on a rocking table at 5 RPM in a humidor. The plate is washed (e.g., 3 times) with washing buffer as known in the art. Then, 100 $\mu$l of appropriately diluted monoclonal or polyclonal reporter antibody (preferably pre-absorbed with the biotinylated antibody used to coat the wells of the plate, e.g., using an avidin column), is added and allowed to incubate at room temperature overnight (i.e., 18–20 hours) or for another incubation period as appropriate. The plate is washed again, as described above, and 100 $\mu$l alkaline phosphatase-conjugated anti-rabbit Ig (commercially available from Pierce) appropriately diluted in blocking buffer (e.g., BSA Blocker in TBS) are added, and allowed to incubate for 2 hours with rocking as described above. The plate is then washed again as described above. The enzyme substrate is added to the wells and the reaction allowed to occur for an appropriate length of time, at the end of which the reaction is stopped as known in the art, and the optical densities of the solutions within the wells determined as known in the art.

Because background signal is often the limiting factor in amplified assays, in some embodiments, measures are undertaken to reduce background signal in these assays. First, the antiserum used for detection of the APP or kinesin-I is reabsorbed by passing it over a streptavidin column to which biotinylated antibody (i.e., the primary antibody) has been coupled. This is done to remove nonspecific reactivity against mouse IgG (i.e., the reporter antibody). Second, in some embodiments, conjugated anti-rabbit-Ig is selected which is been depleted of reactivity with murine and human IgG. Third, biotin/avidin is used to fix the capture antibody to the plate; this in turn allows for more vigorous washing protocols with a detergent-containing buffer. Fourth, efficient blocking reagents (e.g., BSA Blocker and SuperBlock, Pierce) are used.

The assay system outlined above also finds use in the detection of complexes comprising kinesin-I and APP. In these embodiments, the complexes are detected by using either antibodies or ATPase test methods. Thus, in some embodiments, the presence of kinesin-I/APP complexes in a biological sample (e.g., tissues or bodily fluids) is detected. In addition, these methods are useful for determining the ability of test compounds to inhibit or prevent the ATPase reaction from occurring in the sample. Thus, the present invention provides various methods to assess the binding of APP and kinesin-I and the effects of inhibitors on this binding and/or the consequences of this binding.

In addition to standard indirect and direct immunoassay methods, competitive assays are provided by the present invention. Such competitive assays find use in the detection of compounds that inhibit the interaction (i.e., binding) of APP and kinesin-I. Thus, in these assays, a known concentration of APP or kinesin-I is used to coat the wells of an ELISA plate, and a test compound is added to the wells at about the same time as a known concentration of kinesin-I or APP is added to the wells. The same washing procedures are used as described above. Binding of APP to kinesin-I is then detected using an antibody directed against either kinesin-I or APP, whichever compound is being detected in the test sample (i.e., is different from the compound used to coat the wells of the plate). In preferred embodiments, the tests are run using dilution series of the various reagents (i.e., a titration checkerboard is used). The test compound is then analyzed for its ability to modulate the binding of APP to kinesin-I. Test compounds identified as inhibiting the binding of APP to kinesin-I are then further analyzed. Test compounds that enhance the binding of APP to kinesin-I are are also further analyzed. In some cases, test compounds that have no effect on the binding of APP to kinesin-I are also further analyzed. Thus, the screening methods of the present invention provide means to identify compounds that modulate the binding of APP to kinesin-I and are useful in the treatment and/or prevention of Alzheimer's disease.

Solution-Based Assay Systems

In addition to the assay systems in which a solid support is utilized, the present invention provides methods in which the assay components remain suspended in solution. In these embodiments, the presence of APP binding to kinesin-I is detected by an increase in ATPase activity. Such ATPase methods are also known in the art (See e.g., Huang and Hackney, J. Biol. Chem., 269:16493 [1994]; as well as Sakowicz et al., Science 280:292–295 [1998]). In some embodiments of these methods, basal ATPase activity is stimulated, while in other embodiments, microtubule-stimulated ATPase activity is involved. Indeed, it is not intended that the present invention be limited to any particular assay system or test conditions.

As with the solid phase assay systems, competitive assays are provided by the solution-based methods of the present invention. Such competitive assays find use in the detection of compounds that inhibit the interaction (i.e., binding) of APP and kinesin-I, as indicated by a reduction in ATPase stimulation. Thus, in these assays, known concentrations of APP and kinesin-I are mixed together in the presence of a test compound. Binding of APP to kinesin-I is then detected based on the stimulation of ATPase activity. In preferred embodiments, the tests are run using dilution series of the various reagents (i.e., a titration checkerboard is used). The test compound is then analyzed for its ability to modulate the binding of APP to kinesin-I. Test compounds identified as inhibiting the binding of APP to kinesin-I are then further analyzed. Test compounds that enhance the binding of APP to kinesin-I are are also further analyzed. In some cases, test compounds that have no effect on the binding of APP to kinesin-I are also further analyzed. Thus, the screening methods of the present invention provide means to identify compounds that modulate the binding of APP to kinesin-I and are useful in the treatment and/or prevention of Alzheimer's disease.

EXPERIMENTAL

The following Examples are provided in order to demonstrate and further illustrate certain preferred embodiments and aspects of the present invention and are not to be construed as limiting the scope thereof.

In the experimental disclosure which follows, the following abbreviations apply: ° C. (degrees Centigrade); rpm (revolutions per minute); BSA (bovine serum albumin); CFA (complete Freund's adjuvant); IFA (incomplete Freund's adjuvant); IgG (immunoglobulin G); IM (intramuscular); IP (intraperitoneal); IV (intravenous or intravascular); SC (subcutaneous); $H_2O$ (water); HCl (hydrochloric acid); wt (wild-type); aa (amino acid); bp (base pair); kb (kilobase pair); kD (kilodaltons); gm (grams); μg (micrograms); mg (milligrams); ng (nanograms); μl (microliters); ml (milliliters); mm (millimeters); nm (nanometers); μm (micrometer); M (molar); mM (millimolar); μM (micromolar); U (units); V (volts); MW (molecular weight); sec (seconds); min(s) (minute/minutes); hr(s) (hour/hours); $MgCl_2$ (magnesium chloride); NaCl (sodium chloride); $OD_{280}$ (optical density at 280 nm); $OD_{600}$ (optical density at 600 nm); PAGE (polyacrylamide gel electrophoresis); PBS (phosphate buffered saline [150 mM NaCl, 10 mM sodium phosphate buffer, pH 7.2]); PCR (polymerase chain reaction); PEG (polyethylene glycol); PMSF (phenylmethylsulfonyl fluoride); RT-PCR (reverse transcription PCR); SDS (sodium dodecyl sulfate); Tris (tris (hydroxymethyl)aminomethane); w/v (weight to volume); v/v (volume to volume); AMERSHAM (Amersham Life Science, Inc. Arlington Heights, Ill.); ICN (ICN Pharmaceuticals, Inc., Costa Mesa, Calif.); AMICON (Amicon, Inc., Beverly, Mass.); ATCC (American Type Culture Collection, Rockville, Md.); BABCO (Berkeley Antibody Company (BABCO), Richmond, Calif.); STRESSGEN (StressGen Bioteclnologies Corp., Victoria, BC, Canada); BECTON DICKINSON (Becton Dickinson Labware, Lincoln Park, N.J.); BIORAD (BioRad, Richmond, Calif.); CLONTECH (CLONTECH Laboratories, Palo Alto, Calif.); DIFCO (Difco Laboratories, Detroit, Mich.)); GIBCO BRL (Life Technologies, Inc., Gaithersburg, Md.); QIAGEN (Qiagen, Inc., Valencia, Calif.); INVITROGEN (Invitrogen Corp., San Diego, Calif.); KODAK (Eastman Kodak Co., New Haven, Conn.); NEW ENGLAND BIOLABS (New England Biolabs, Inc., Beverly, Mass.); NOVAGEN (Novagen, Inc., Madison, Wis.); PHARMACIA (Pharmacia, Inc., Piscataway, N.J.); SCHLEICHER & SCHUELL (Schleicher and Schuell, Inc., Keene, N.H.); CHEMICON (Chemicon, Inc., Pittsburgh, Pa.); SIGMA (Sigma Chemical Co., St. Louis, Mo.); SORVALL (Sorvall Instruments, a subsidiary of DUPONT CO., BIOTECHNOLOGY SYSTEMS, Wilmington, Del.); ZYMED (Zymed Labs, South San Francisco, Calif.); JACKSON IMMMUNORESEARCH (Jackson ImmunoResearch Laboratories, Inc., West Grove, Pa.); STRATAGENE (Stratagene Cloning Systems, La Jolla, Calif.); WHATMAN (Whatman LabSales, Hillsboro, Oreg.); AMBION (Ambion, Inc., Austin, Tex.); and ZEISS (Carl Zeiss, Inc., Thornwood, N.Y.).

For Western blots, the monoclonal antibody, 63–90 (See, Stenoien et al., Mol. Biol. Cell., 8:675–689 [1997]), which recognizes KLC1 and KLC2 was used at 1:1000, the polyclonal KIF5A, KIF5B, and KIF5C antibodies were used at 1:100, the APP monoclonal antibody, 22 C11 (CHEMICON) was used at 1:500, the 4G8 APP monoclonal antibody (SYNTEK) was used at 1:500, the tubulin monoclonal antibody (DM1A; SIGMA) was used at 1:5000, the cytoplasmic dynein intermediate chain (DIC) monoclonal antibody (CHEMICON) was used at 1:1000, the GFP monoclonal antibody (CLONTECH) was used at 1:500, the His-tag antibody (QIAGEN) was used at 1:500, the KIF3A monoclonal antibody (K2.4, BABCO) was used at 1:1000, the synaptophysin monoclonal antibody (SY38, BOEHRINGER) was used at 1:200, the GAP43 monoclonal antibody (BOEHRINGER) was used at 1:1000, the synaptotagmin monoclonal antibody (STRESSGEN) was used at 1:500, and the actin monoclonal antibody (SIGMA) was used at 1:5000. The KLC1 and KLC2 specific polyclonal antibodies were previously described (Rahman et al., J. Biol. Chem., 273:15395–15403 [19981]). The C-terminal APP polyclonal antibody was from CHEMICON (AB5352). The KLC-A11 monoclonal antibody a generous gift from Scott Brady (Stenoien et al., [1997], supra).

EXAMPLE 1

KLC1 Gene Targeting and Chimeric Mouse Production

In this Example, methods for KLC1 gene targeting and mutant mouse production are described. A 129 isogenic genomic library (obtained from Dr. A. Nagy, Samuel Lunenfeld Research Institute, Toronto, Canada) was screened with the full-length KLC1 cDNA as known in the art (See e.g., Rahman et al., [1998], supra).

Various genomic clones were characterized by restriction digestion followed by Southern analysis. One clone, g5.1, was determined to contain the translational start site. This clone was further characterized by extensive restriction digests and partial sequencing. A 2.5-kb HindIII/PstI genomic fragment was sub-cloned into pBS II KS (2; STRATAGENE) as the 39 flanking arm (pBS-39). A 1.4-kb BglII/NotI subcloned fragment was digested with EcoRV and Eco0109, and the smaller 1.2-kB fragment was blunted with Klenow and subsequently subcloned into the XhoI site of pBS-39. The resulting targeting construct (pBS-59139) had both the 59 and 39 flanking arms and unique SalI and NotI sites. The exon that was removed encoded a 72 amino acid sequence starting at QHSDSSA (SEQ ID NO:1) and ending at NILALVY (SEQ ID NO:2).

Figure 1A:
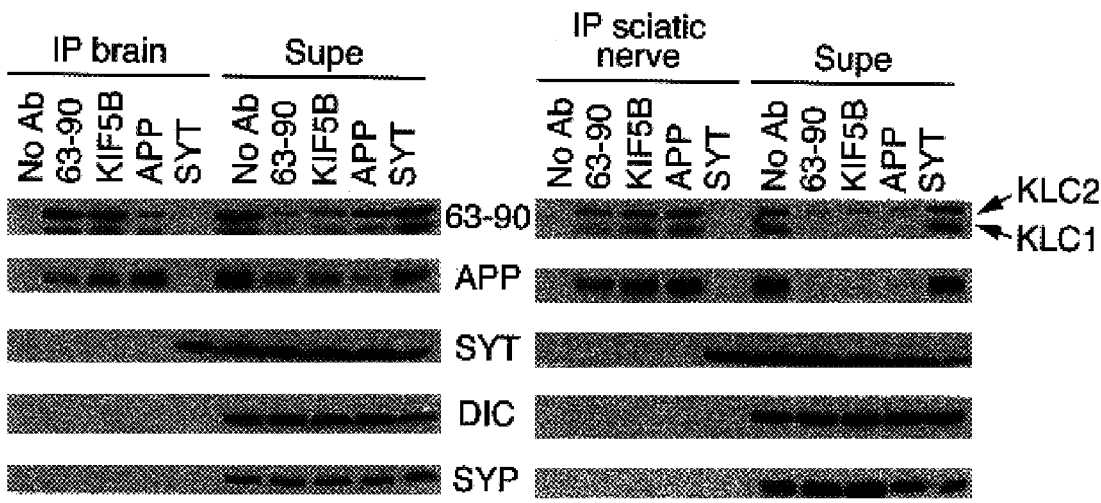
FIGS. 1A–C provides immunoblot for various experiments. Panel A provides results showing co-immunoprecipitation of APP with kinesin-I subunits from mouse brain and sciatic nerve extracts. Mouse brain (left side of panel; IP brain) or sciatic nerve (right side of panel; Supe) extracts were immunoprecipitated with a no antibody control (No Ab), the 63–90 antibody (which recognizes both KLC1 and KLC2; i.e., kinesin light chains 1 and 2), antibodies to KIF5B (ubiquitous KHC), or APP (C-terminal polyclonal antibody) or synaptotagmin (SYT). Panel B provides results showing the specificity of kinesin-I co-immunoprecipitation with APP. Co-immunoprecipitation of APP with KLC from wild-type (wt) and mutant (−/−) KLC1 brain extracts was done using 63–90 or antibodies specific to either KLC1 or KLC2, and then analyzed by Western blots using either 63–90 or APP (22C11) antibodies. Panel C provides results showing KLC1 dependence of KHC complexes with APP. Co-immunoprecipitation of APP with KHC from wild-type (wt) and mutant (−/−) KLC1 brain extracts were performed using antibodies to three different KHC subunits (KIF5A, KIF5B and KIF5C), and then analyzed by Western blots using either 63–90 or APP (22C11) antibodies, as shown in this Panel.

This region contained genomic sequences encoding the 10 amino acids before the beginning of the first TPR (tetratrico peptide repeat) domain, the entire first TPR domain, and 20 amino acids of the second TPR domain (See, Rahman et al., [1998], supra). It is contemplated that removal of this segment of genomic DNA results in out of frame translation of the remainder of the KLC1 gene (See e.g., FIG. 1A of Rahman et al., [1999], supra). The 6-kB SalI fragment of pGT-IRES β-geo (Mountford et al., Proc. Natl. Acad. Sci. USA 91:4303–4307 [1994]), containing the IRES β-geo cassette, was subcloned into pBS-59139 to complete the targeting construct (See, FIG. 1A of Rahman et al., [1999], supra).

The targeting vector was linearized using the unique NotI site, and 20 mg of the linearized DNA was electroporated into R1 embryonic stem (ES) cells as described by Wurst and Joyner (Wurst and Joyner, in Joyner (ed.), *Gene Targeting: A Practical Approach*, Oxford University Press, New York, [1993], pp. 32–61). The ES cells were grown (Wurst and Joyner, supra) for 2 d before selection with 125 mg/ml of G418 (active weight; GIBCO BRL) for an additional 10 d. 94 ES cell colonies were isolated and the fastest growing 67 colonies were checked by PCR for a homologous recombination event. The 5' PCR primer (CTAATTTTGGACTTCCAGCAAAGAC; SEQ ID NO:3)) encoded KLC1 genomic DNA sequences residing outside the targeting vector. The 3' primer (TACACCTGGCCAGTGAGGCTTCTA; SEQ ID NO:4), used for PCR, encoded sequences within the en-2 region of the IRES β-geo cassette. The resulting PCR product was approximately 1.4 kb. Of the initial 67 clones checked, 6 gave PCR products of the expected size.

These clones (A1, A2, E2, F1, F11, and H4) were verified as homologous recombinants by Southern analysis of SacI digested genomic DNA. The probe used was a 240-bp SacI/BglII fragment adjacent to the targeted sequences. Clones that tested positive for recombination events were trypsinized to single cell state and microinjected into 3.5-d C57BL/6 embryos to produce chimeric mice.

EXAMPLE 2

Co-Immunoprecipitation and Western Blot Analyses

In this Example, the co-immunoprecipitation and Western blot analyses conducted during the development of the present invention are described.

A. Co-immunoprecipitation

Co-immunoprecipitation from wild-type and mutant KLC1 (See e.g., Rahman et al., J. Cell Biol., 146:1277–1288 [1999]) mouse littermate brain extracts and sciatic nerve extracts was conducted as known in the art (See e.g., Rahman et al., [1990], supra) using NP-40 lysis buffer (1% NP-40, 150 mM NaCl, 50 mM Tris, pH 8.0) as the homogenization buffer.

In addition, extracts from normal CHO cells, and the wild-type full-length APP overexpressing CHO cells, and the C-terminal deleted APP overexpressing CHO cells (obtained from E. Koo, University of California, San Diego) were prepared by homogenizing in NP-40 lysis buffer and co-immunoprecipitations done as previously described (Rahman et al., [1999], supra).

The immunoprecipitation reactions were carried out as described by Rahman et al. (1998). Briefly, whole brains from 6-wk-old wild-type, heterozygous, and homozygous mice were homogenized in 1 ml P-40 lysis buffer (1% NP-40, 150 mM NaCl, 50 mM Tris, pH 8.0). The homogenates from brain from each type of mouse were spun at 100,000×g for 30 min to yield lysate. Then, 100 ml of lysate was precleared with preblocked protein A-Sepharose beads (ZYMED) and subsequently used for immunoprecipitation reactions.

Sufficient quantities of either anti-KLC1 and anti-KLC2 (Rahman et al., [1998], supra), or anti-KIF5A and anti-KIF5B antibodies (Niclas et al., Neuron 12:1059–1072 [1994]) were added to the precleared lysate so as to completely immunoprecipitate the antigens in the lysate. Although no protease inhibitors were used in these particular experiments, it is contemplated that such inhibitors will be included in the assay system, as needed or desired. The antibody-protein complex was precipitated with protein A-Sepharose beads (ZYMED). The beads were washed several times with RIPA buffer (150 mM NaCl, 50 mM Tris, pH 8.0, 1% NP-40, 0.5% deoxycholate, 0.1% SDS), once with 50 mM Tris, pH 6.8, and resuspended in 23 SDS loading buffer. Equivalent volumes of lysates and immunoprecipitates, and supernatants from immunoprecipitates were loaded in each lane and subsequently analyzed by Western blotting as described below.

B. Western Blotting

Briefly, a whole brain from 6-wk-old wild-type, heterozygous, or homozygous mouse was homogenized in PBS (140 mM NaCl, 2.5 mM KCl, 10 mM Na-phosphate dibasic, 2 mM K-phosphate monobasic, pH 7.4) with protease inhibitors. The crude lysate was centrifuged at 3,000×g and the supernatant quantitated for total amount of protein by Bradford analysis (BIORAD). Equivalent amounts of total protein were loaded per lane on 10% polyacrylamide gels. Western analysis was done with monoclonal antibody 63–90 (1:1,000 dilution of ascites fluid; See e.g., Stenoinen and Brady, Mol. Biol. Cell 8:675–689 [1997]), polyclonal antisera directed against KLC1 and KLC2 (Rahman et al., [1998], supra), polyclonal antisera directed against KIF5A (1:100 dilution), polyclonal sera directed against KIF5B (1:1,000 dilution; Niclas et al., Neuron 12:1059–1072 [1994]), or a monoclonal antibody directed against actin (1:5,000 dilution; BOEHRINGER Catalog #1 378 996). Bands were visualized by incubating with either HRP-conjugated goat anti-rabbit IgG (ZYMED) or goat anti-mouse IgG (JACKSON IMMUNORESEARCH) secondary antibodies, and subsequent processing with ECL (NYCOMED AMERSHAM INC.).

C. Quantitative Western Blotting

For quantitative Western blot analysis of protein amounts, the antibodies were first calibrated to give linear detection of signals over a linear dilution range (10–50 μg of the brain supernatant/lane. Equal amounts (40 μg) of brain supernatant were loaded for the wild-type, heterozygous, and mutant KLC1 samples and probed with the above antibodies. Band intensities were quantitated using NIH Image and relative ratios of the intensities were calculated.

Figures 1B, 1C:
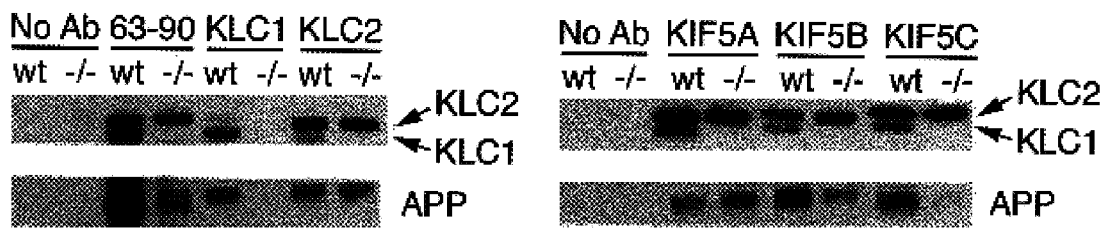

As indicated in FIG. 1, Panel A, in brain and sciatic nerve extracts, both kinesin-I antibodies co-immunoprecipitated APP in addition to kinesin-I subunits. In contrast, the no antibody controls or a synaptotagmin antibody, brought down no detectable APP or kinesin-I. In the complementary co-immunoprecipitation experiment, a polyclonal anti-APP antibody directed against the last nine residues of the C-terminus of APP precipitated significant amounts of APP and kinesin-I subunits.

To test further the specificity of the co-immunoprecipitations, the immunoprecipitates were also probed with antibody probes recognizing synaptotagmin and synaptophysin, which are synaptic vesicle membrane proteins proposed to be cargoes for a different kinesin superfamily motor called UNC104/KIF1A (See, Okada et al., Cell 81:769–780 [1995]; Otsuka et al., Neuron 6:113–122 [1991]; and Yonekawa et al., J. Cell Biol., 141:431–441 [1998]), and for the retrograde motor dynein. None of these proteins co-immunoprecipitated with kinesin-I or APP, thus demonstrating the specificity of the co-immunoprecipitations between kinesin-I and APP. Addition of 500 mM NaCl to the immunoprecipitation experiments had no apparent effect on the observed co-immunoprecipitation of APP and kinesin-I (data not shown) indicating that this interaction is relatively robust.

In addition, the observation was made that a prominent difference between the co-immunoprecipitations from brain versus sciatic nerve extracts was that in the sciatic nerve extracts, a substantially larger fraction of the APP was brought down relative to the brain extracts. Since the sciatic nerve is highly enriched for sensory and motor nerve axons and lacks nerve cell bodies (although Schwann cells and a few other non-neuronal cell types are present), it is relatively enriched in the actively moving component of neuronal cargoes. Thus, it is contemplated that much of the APP in the actively transported compartment of neurons exists in a transport complex with kinesin-I whereas in whole brain there may be pools of APP that are pre- or post-transport and therefore not associated with kinesin-I. However, an understanding of the mechanism(s) is not necessary in order to use the present invention.

To further evaluate the specificity of the co-immunoprecipitation experiments, similar experiments were conducted using brain extracts made from a gene-targeted mouse mutant of KLC1 (See, Rahman et al., [1999], supra). The results of these experiments are shown in FIG. 1, Panel B. As indicated in this Figure, the 63–90 antibody immunoprecipitated significantly less APP from the mutant KLC1 mouse brains compared to the wild-type. Since the 63–90 antibody brings down both KLC1 and KLC2, co-immunoprecipitation experiments were also conducted with antibodies specific for either KLC1 or KLC2 (See, Rahman et al., [1998], supra). As expected, the KLC1 antibody brought down APP in wild-type, but not in mutant KLC1 mice. The KLC2 antibody immunoprecipitates equivalent amounts of APP in wild-type and mutant KLC1 mice, indicating that APP can interact with KLC2 as well as KLC1.

To confirm that APP can interact with both KLC1 and KLC2, three KHC antibodies (KIF5A, KIF5B, and KIF5C) were used to co-immunoprecipitate APP from wild-type and mutant KLC1 brain extracts. The results of these experiments are shown in FIG. 1, Panel C. Although all three KHC antibodies were able to co-immunoprecipitate APP from both genotypes, the amount of APP associated with KIF5B was found to be slightly reduced in the KLC1 mutant, whereas there is a significant decrease in the amount of APP that comes down with the KIF5C antibody. The amount of APP that came down with KIF5A was unchanged in wild-type versus the KLC1 mutant. These results suggest that association of KIF5B or KIF5C with APP depends to a greater extent on KLC1 than KLC2, while association with KIF5A depends to a greater extent upon KLC2 than KLC1. Taken together, however, the data support the conclusion that co-immunoprecipitation of kinesin-I and APP is due to the formation of a complex in vivo, as opposed to non-specific contamination of immunoprecipitates by APP, and that APP interacts with both KLC1 and KLC2. Intriguingly, these data suggest that the interaction of kinesin-I with APP might vary among different combinations of KHC and KLC subunits.

Figure 4:
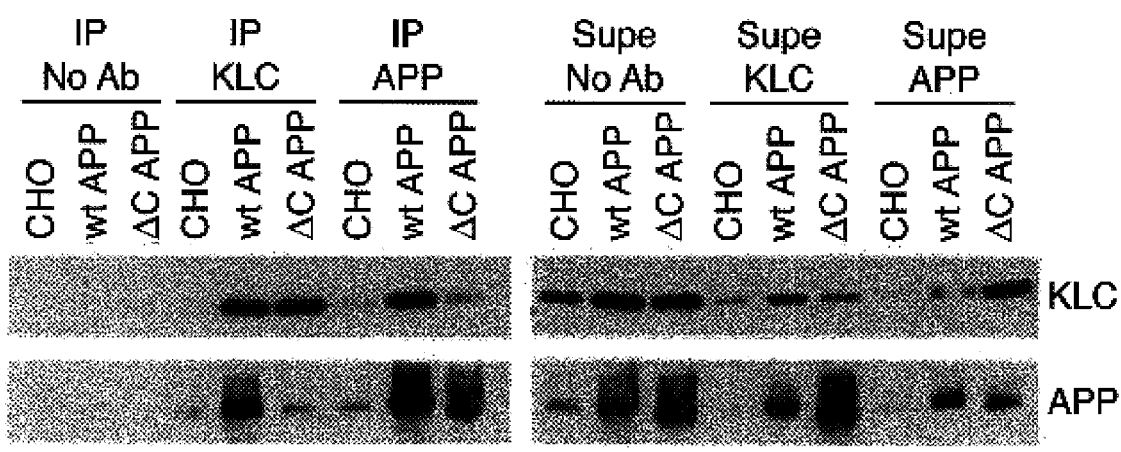
FIG. 4 provides results showing that the C-terminus of APP is required for complex formation with kinesin-I. Cell lysates from normal CHO cells (CHO) or CHO cells over-expressing wild-type full-length APP (wtAPP) or a C-terminal deletion of APP (ΔCAPP) were immunoprecipitated with either no antibody control or antibodies recognizing KLC (63–90) or APP (22C11). Equal amounts of the immunoprecipitate (IP) and the remaining supernatant (Supe) were loaded onto SDS-PAGE gels, and then analyzed by Western blots using KLC (63–90) and APP (22C11) antibodies. For the KLC blot, we show an exposure selected to minimize overexposure of the bands from wtAPP and ΔCAPP CHO cells. The KLC band from the normal CHO cells immunoprecipitated with KLC antibody is thus faint and appears only on a longer exposure (data not shown).
Figure 5A:
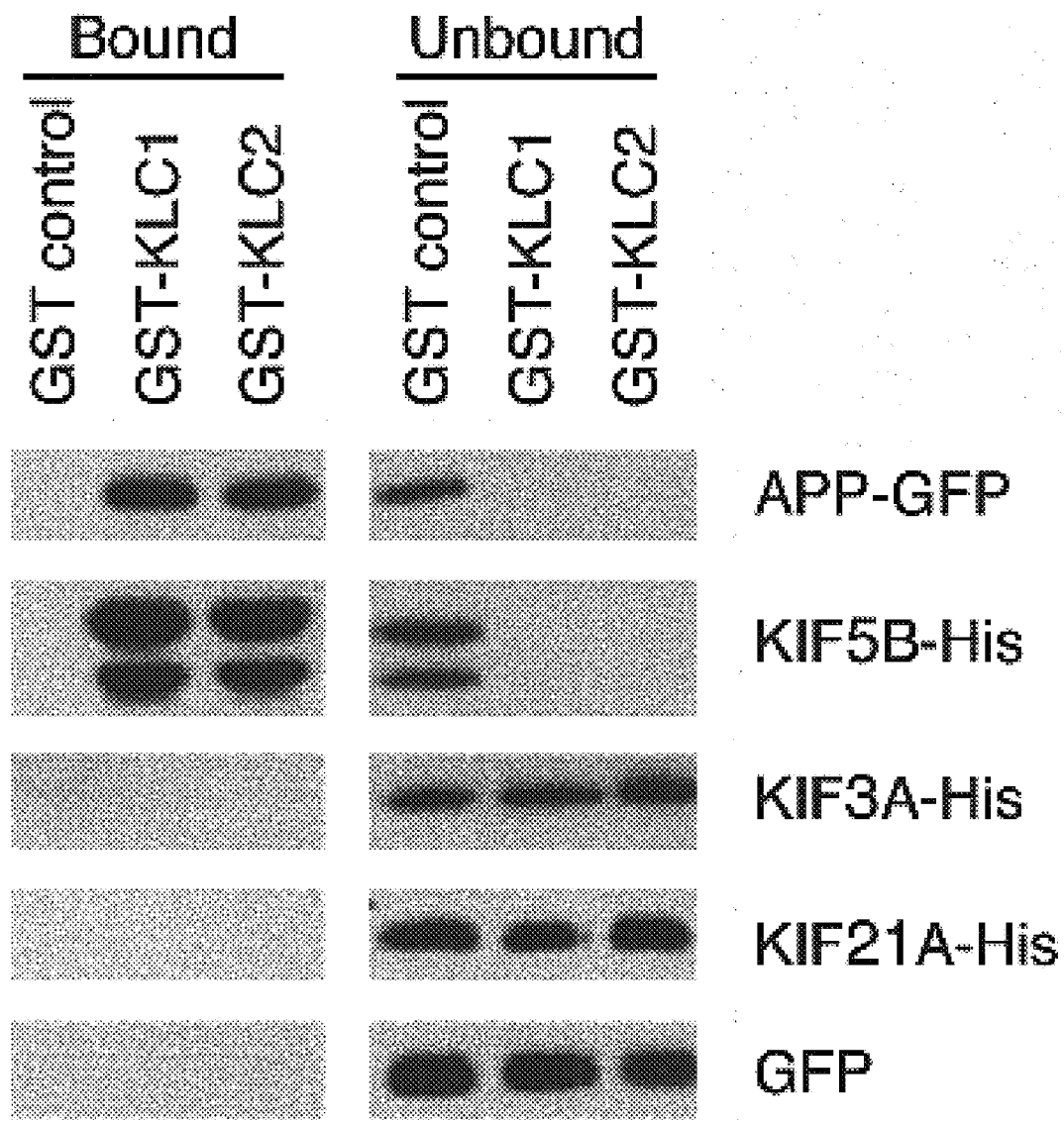
FIGS. 5A–E provides results showing the direct binding of the C-terminal tail of APP to the TPR domain of KLC. Panel A provides a Western blots showing that the C-terminus of APP directly binds KLC. Purified GST, GST-KLC1 and GST-KLC2 bound to glutathione agarose beads were incubated with purified fusion proteins consisting of the C-terminal tail of APP (APP-GFP), KIF5B (KIF5B-His), KIF3A (KIF3A-His), KIF21A (KIF21A-His), or GFP alone. The unbound protein was saved, and the beads were washed and bound proteins eluted with glutathione. The bound and unbound proteins were analyzed by SDS-PAGE followed by Western blotting with antibodies to either GFP or the His-tag. For KIF5B-His, the lower band is a degraded product that still retains the KLC binding site. Panel B provides results of experiments to determine the binding of APP C-terminus to KLC1. Increasing amounts of APP-GFP were added to 60 nM GST-KLC1 and the $K_d$ determined by curve-fitting as described in the Examples. Also shown are predicted curves for cases where $K_d=1$ nM or 50 nM. Panel C provides results from binding analysis of APP C-terminus to KLC2. Increasing amounts of APP-GFP were added to 60 nM GST-KLC2 and the $K_d$ determined by curve-fitting as described in the Examples. Also shown are predicted curves for $K_d=1$ nM or 50 nM. Panel D provides results indicating that a monoclonal antibody to the TPR domain of KLC (KLC-A11) inhibits APP binding to KLC. Binding of purified GST, GST-KLC1 and GST-KLC2 to APP-GFP in the presence of no antibody or monoclonal KLC-A11 (IgG$_1$) or monoclonal 63–90 (IgG$_1$) antibodies. Bound and unbound proteins were analyzed as above using the GFP antibody.
Figure 5C:
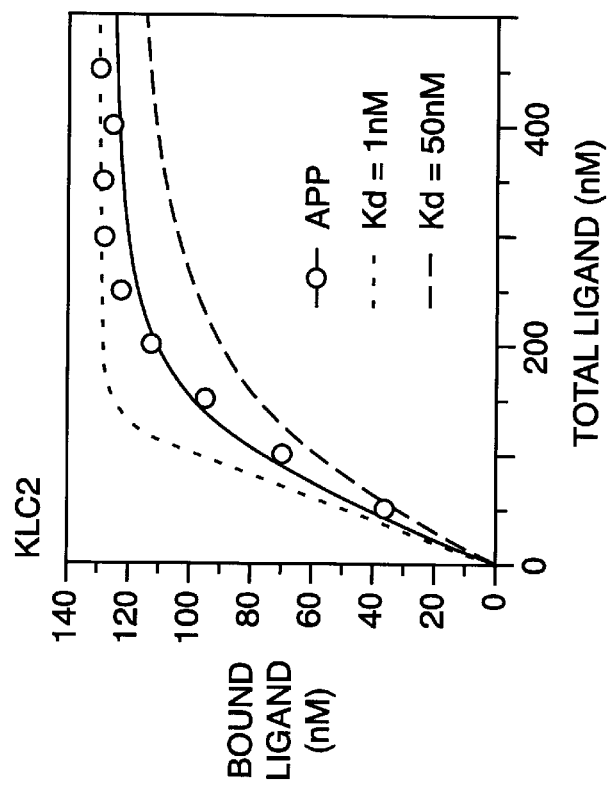
Figure 5B:
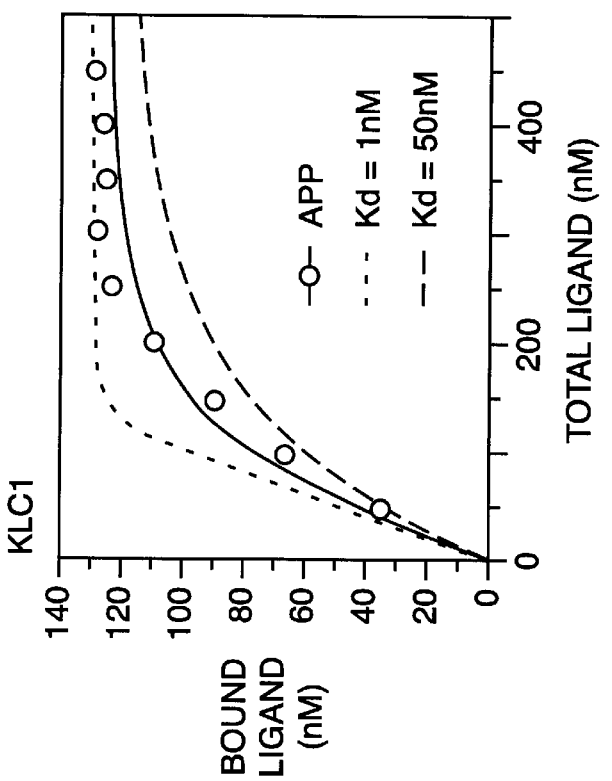
Figure 5D:
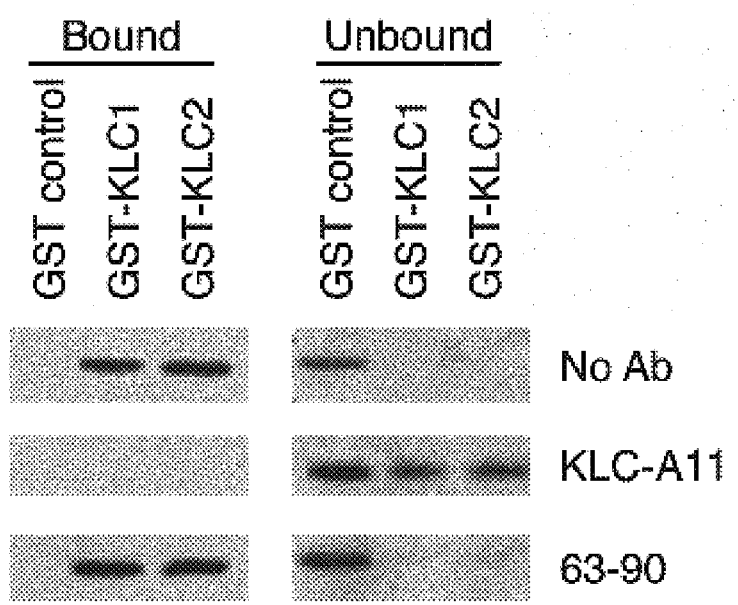
Figure 5E:
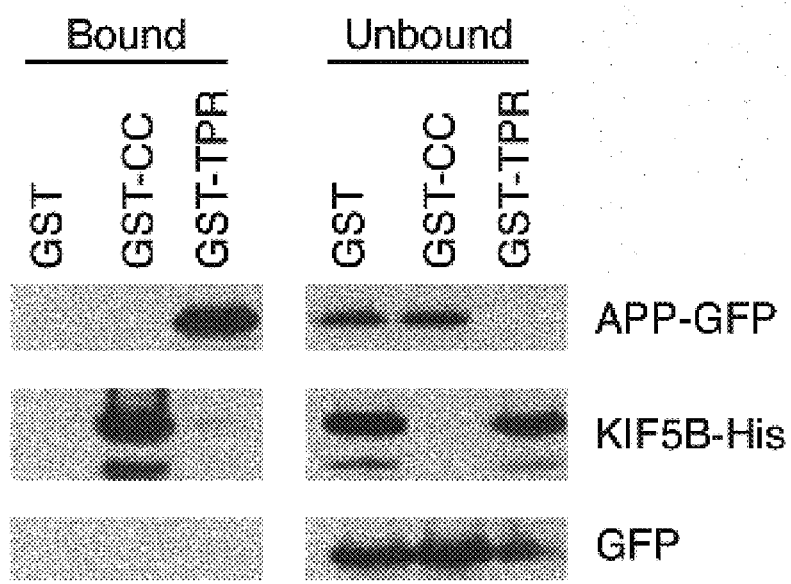

In addition to the experiments using wild-type and mutant mice, described above, experiments were conducted in order to determine whether the cytoplasmic C-terminal domain of APP was necessary for the interaction of APP with kinesin-I, co-immunoprecipitation experiments from extracts of normal CHO cells or CHO cells overexpressing wild-type full-length APP (wtAPP) or a C-terminal deletion of APP (ΔCAPP lacking 43 amino acids from the 47 amino acid cytoplasmic domain) (Perez et al., J. Biol. Chem., 274:18851–18856 [2000]) were conducted. The results of these experiments are shown in FIG. 4.

Antibodies to KLC (63–90) co-immunoprecipitated a substantial fraction of APP (compare IP versus supernatant in FIG. 4) from normal CHO cells and wtAPP CHO cells. In contrast, only a small amount of APP was co-immunoprecipitated from the ΔCAPP CHO cells. The amount observed from the ΔCAPP CHO cells is comparable to the amount co-immunoprecipitated from control CHO cells, and is most likely to be the endogenous full-length APP based on its slightly slower mobility than the ΔCAPP. The no antibody control did not co-immunoprecipitate any detectable APP. In a complementary experiment, using the APP antibody 22C11, a small amount of KLC was co-immunoprecipitated from normal CHO cells and a larger amount from the wtAPP CHO cells; only amounts comparable to normal cells were co-immunoprecipitated from the ΔCAPP CHO cells. Thus, these results indicate that the C-terminus of APP is necessary for complex formation with the KLC subunit of kinesin-I.

EXAMPLE 3

Sucrose Gradient Analysis

Sucrose gradient analyses of mouse brain membrane associated proteins was done with minor modifications to the protocol described previously (Rahman et al., [1999], supra). Briefly, mouse brains from wild-type and mutant KLC1 littermates were homogenized in Buffer A (10 mM HEPES, pH 7.3, 0.5 mM EGTA, 0.5 mM EGTA, 0.5 mM $MgCl_2$, 50 μM ATP) without detergent, and spun at 100,000×g; the pellets were then solubilized in Buffer A+0.5% NP-40 and spun at 100,000×g, and the resulting supernatant was top-loaded onto a 5–20% linear sucrose gradient, fractions were collected and protein samples analyzed by quantitative western blotting as described in Example 2. Control protein markers, alcohol dehydrogenase (7.4 S), catalase (11.3 S), and b-galactosidase (16 S) were solubilized and centrifuged in parallel sucrose gradients, and the enzymatic activities measured in each fraction as known in the art (See e.g., Martin and Ames, J. Biol. Chem., 236:1372–1379 [1961]) to determine the peak of each marker.

Figure 2:
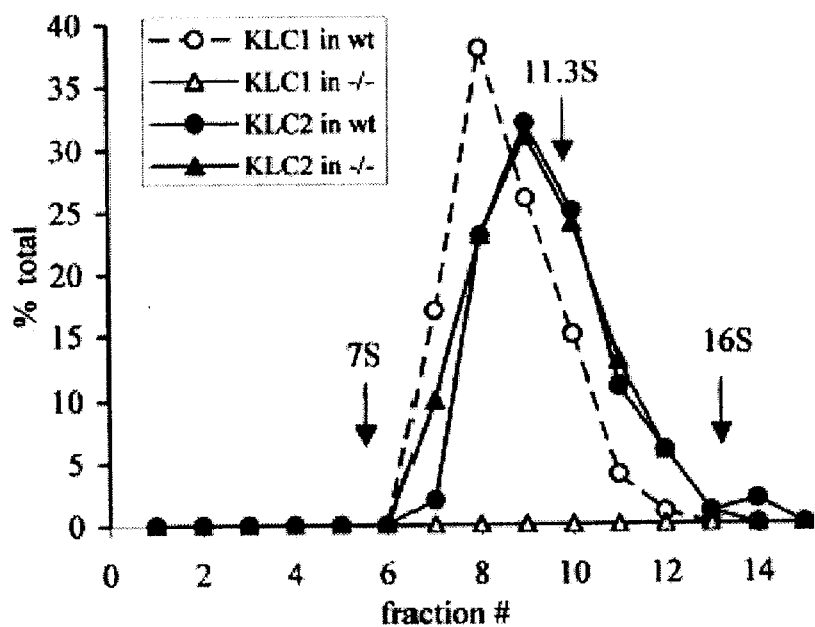
FIGS. 2A–B provides results showing that co-sedimentation of APP with KLC1 in sucrose gradients is disrupted in the KLC1 mutant. Membrane-bound proteins from wild-type (wt) and mutant (−/−) KLC1 mouse brains were top-loaded onto 5–20% linear sucrose gradients to separate protein complexes by velocity sedimentation. Fractions were collected and protein samples analyzed by quantitative Western blotting using antibodies to KLC (63–90), as shown in Panel A, and APP (22C11), as shown in Panel B. The percentage of total KLC1, KLC2, and APP in each fraction was calculated for wild-type (circles) and mutant (triangles) KLC1 sucrose gradients. Control protein markers were run in parallel gradients; the enzyme activity of alcohol dehydrogenase (7S) was at fraction 6, catalase (11.3S) was at fraction 9–10, and β-galactosidase (16S) was at fraction 13–14 (data not shown).
Figure 2:
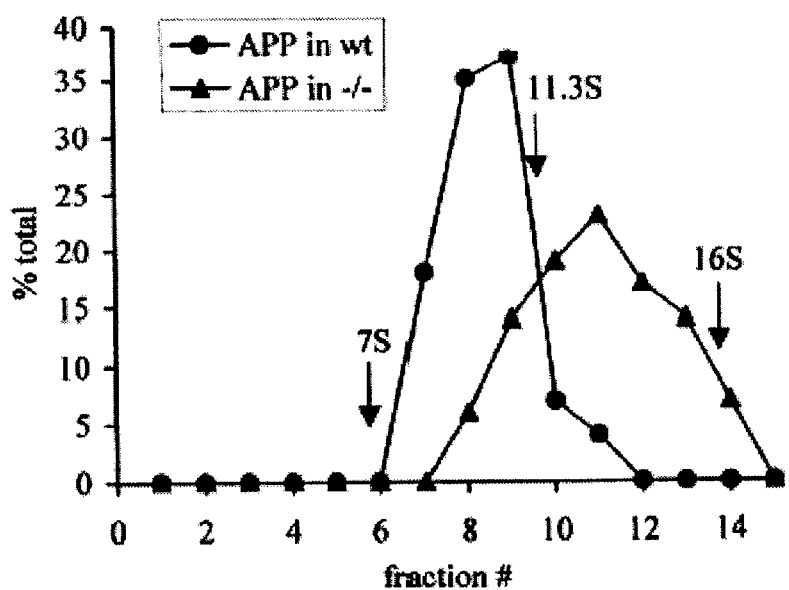

FIG. 2 provides the results of these sucrose gradients experiments conducted on membrane proteins from mouse brain extracts. As indicated in this Figure, when wild-type gradient fractions from mouse brain were probed with the KLC antibody 6390, the KLC1 peak migrated around 9 S (fractions 7–9), whereas the KLC2 peak migrated around 10.7S (fractions 8–10) as previously reported (Rahman et al., [1999], supra). Interestingly, similar to KLC1 and KLC2, APP also peaked around 9S to 10S in wild-type mouse brain extracts, overlapping both KLC1 and KLC2.

In contrast, in the KLC1 mutant, APP shifted to a higher sedimentation velocity that overlaps substantially with KLC2, indicating that in the absence of KLC1, there is a shift to an association primarily with KLC2. The KLC2 profile was unchanged in the mutant compared to wild-type as previously reported (Rahman et al., [1999], supra). To ensure that the sedimentation profile was not changed for all proteins in the gradients from the KLC1 mutant, two other membrane proteins (synaptotagmin and synaptophysin) were also probed in these gradients. The results indicated that these were unchanged from wild-type (data not shown). It is interesting that soluble kinesin has been previously reported to exist in two forms: a 6S form (activated and unfolded) and a 9S form (repressed and folded) (Hackney et al., J. Biol. Chem., 267:8696–8701; and Stock et al., [1999], supra). However, the results reported herein indicate that the APP-KLC complex extracted from membrane fractions that sediments at 9S is a shifted 6S complex, thus explaining why the complex is running at the same position as the soluble kinesin-I at 9S. Consistent with this view, it was possible to co-immunoprecipitate a substantial amount of APP with the KLC antibody (63–90) from fraction 8 in wild-type, but only very little from fraction I1. In contrast, although it was possible to co-immunoprecipitate a substantial amount of APP from fraction 11 of KLC1 mutant gradients with the KLC antibody, it was not possible to co-immunoprecipitate appreciable amounts of APP from fraction 8 of KLC1 mutant gradients (data not shown).

EXAMPLE 4

Microtubule Binding Assays

In this Example, microtubule binding assays done to assess whether APP can associate with microtubules and whether this interaction was dependent on KLC are described. These experiments involved in vitro microtubule binding assays from detergent-treated extracts of wild-type and mutant KLC1 mouse brains as previously described (Hanlon et al., Neuron 18:439–451 [1997]) except mouse brains from wild-type and mutant KLC1 littermates were used.

Briefly, mouse brains were homogenized in PEM Buffer (80 mM PIPES, pH 6.8, 2 mM $MgCl_2$, 2 mM EGTA) containing 1% TX-100 and protease inhibitors (10 mg/ml each of leupeptin, and pepstatin), and 1 mM DTT. The homogenate was spun at 45,000 rpm for 30 minutes at 4° C. in a Sorval Ti1270 fixed-angle rotor. The high-speed supernatant (HSS) was collected and the microtubules stabilized by the addition of 40 μM taxol and 1 mM GTP, and incubating for 15 minutes at 37° C. Either 2 mM ATP or 2 mM AMP-PNP was added and further incubated for 15 minutes at 37° C. The microtubules and associated proteins were pelleted by centrifugation at 25,000 rpm in the Sorvall Ti1270 rotor for 30 minutes at 37° C. Equal volumes of the supernatant and pellet suspensions were analyzed using SDS-PAGE and Western blot analysis.

Figure 3:
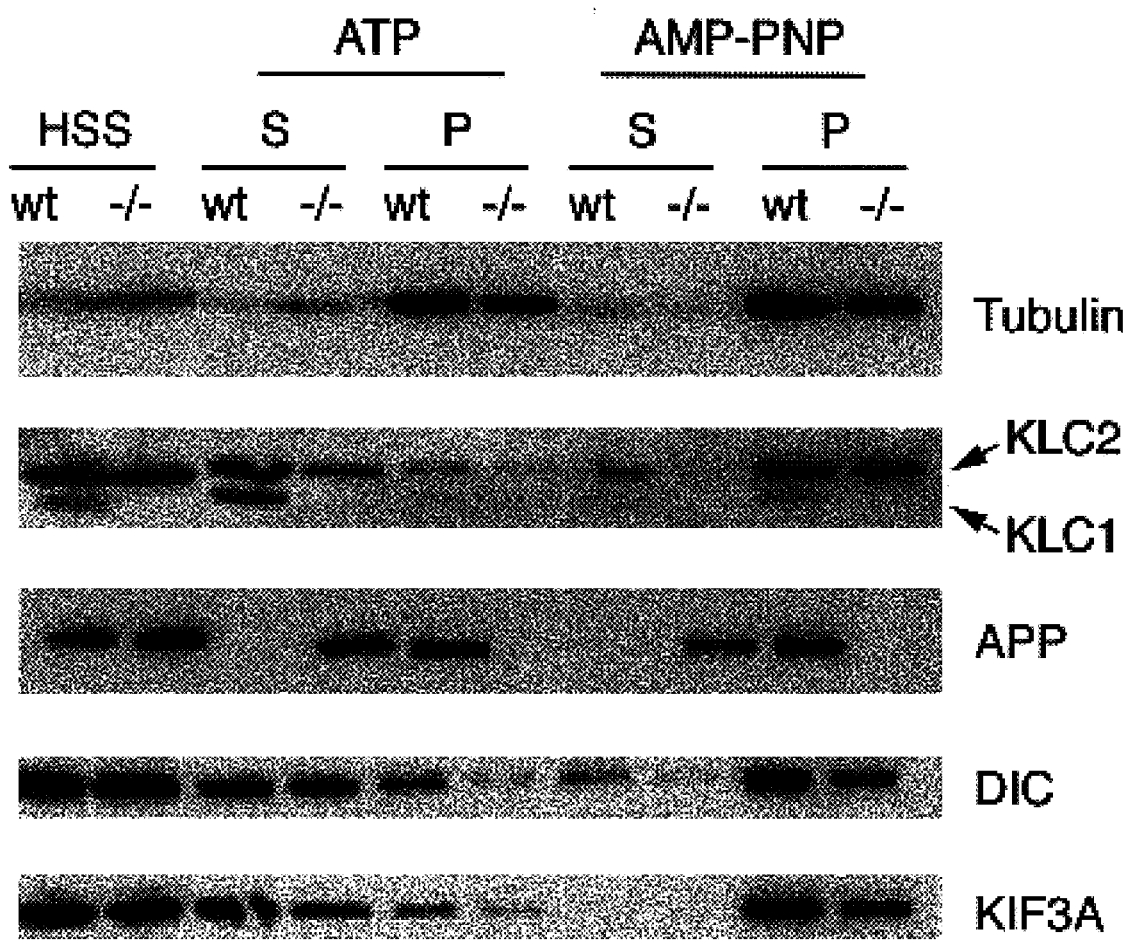
FIG. 3 provides results showing that binding of APP to microtubules depends on KLC. Microtubules were polymerized from wild-type (wt) or mutant (−/−) mouse brain extracts (HSS) containing both soluble and membrane-bound proteins. Either 2 mM AMP-PNP or 2 mM ATP was included. Microtubules and associated proteins were pelleted by centrifugation and equal volumes of pellet (P) containing microtubule associated proteins and supernatant (S) were analyzed by Western blotting using antibodies to tubulin, KLC (63–90), APP (22C11), dynein intermediate chain (DIC) and KIF3A.

The results of these in vitro microtubule binding assays from detergent-treated extracts of wild-type and mutant KLC1 mouse brains are shown in FIG. 3. These extracts contain both soluble and membrane proteins. Consistent with previous experiments, three independent microtubule motors, kinesin-I (detected with KLC antibodies), kinesin-II (detected with KIF3A antibody), and cytoplasmic dynein (detected with a dynein intermediate chain antibody), exhibited greater binding to microtubules in the presence of AMP-PNP than ATP; very little of each motor protein was observed in the AMP-PNP supernatant. There were no discernible differences in the microtubule-binding behavior of the three microtubule motors in the KLC1 mutant except, as expected, KLC1 itself was absent in the mutant.

Examination of APP revealed that it sedimented with microtubules, both in the presence of ATP and AMP-PNP in the wild-type mouse brain extracts. Strikingly, APP did not co-sediment with microtubules in the presence of ATP or AMP-PNP in the mutant KLC1 mouse brain extracts. Although it is unclear why APP associates with microtubules in the presence of ATP, it is possible that APP preferentially associates with the small fraction of kinesin-I that is routinely observed to bind microtubules even with ATP present. Nonetheless, together these results indicate that the association of APP with microtubules is strongly dependent on KLC. In addition, an understanding of the mechanism(s) is not necessary in order to use the present invention.

It was surprising that the relative dependence of APP association with microtubules upon KLC1 and KLC2 is different than might be expected from the co-immunoprecipitation experiments, which suggest that both KLC1 and KLC2 can exist in a complex with APP (See e.g., FIG. 1, Panel B). It is possible that in vivo there exist different functional pools of APP associated with KLCs.

EXAMPLE 5

GST Fusion Proteins

In this Example, experiments conducted to produce GST fusion proteins (GST, GST-KLC1, and GST-KLC2) are described. These fusion proteins were produced and purified as previously described (Rahman et al., [1998]).

Briefly, an NcoI/XhoI fragment of KLC1, which accounts for all but the first seven amino acids of the sequence, was subcloned into pGEX-KG (31) to produce a glutathione S-transferase (GST)-tagged fusion protein. An XhoI/SacI (1784-bp) fragment of KLC2, which accounts for all of the coding sequence from the largest clone (591 amino acids) from the cDNA library, was also subcloned into pGEX-KG to make a GST fusion protein. Recombinant KLC1 and KLC2 protein were overexpressed by induction of transformed BL21 (DE3) bacteria at log phase with 0.2 mM isopropyl-1-thio-b-D-galactopyranoside for 3 h. Recombinant proteins were obtained by lysing the bacterial pellet with French press (1000 p.s.i.) and purifying the supernatant from a 15,000 rpm centrifugation (SS34 rotor, SORVALL) on a glutathione-agarose (SIGMA) column. Recombinant KLC1 and KLC2 were eluted from the glutathione-agarose column with excess glutathione (15 mM) and run on SDS-PAGE.

The GST fusion proteins of the TPR domains (GST-IPR) contained amino acids 167541 of KLC1 whereas the GST fusion protein containing the N-terminal coiled coil domain of KLC (GST-CC) contained amino acids 30–200; both were purified as previously described above. The APP-GFP fusion protein construct contained the C-terminal 42 amino acids of human APP (APP cDNA provided by T. Saitoh) and was generated in a His-tagged pRSETb-EGFP vector, as known in the art. The KIF5B-His fusion protein construct contained the amino acids 499–783 of K1F5B, the KIF3A-His fusion protein contained amino acids 560–709, the KIF21A-His fusion protein contained amino acids 1124–1355, and all three were generated in pET-23b (NOVAGEN). All the fusion proteins were expressed in bacteria and purified by Ni-NTA-agarose as previously described (Marszalek et al., J. Cell Biol., 145469–479 [1999]).

Briefly, in this purification, cells were lysed three times with a French press and then spun for 45 min at 30,000 rpm in a 647.5 Sorvall rotor at 48° C. The fusion proteins were isolated by incubating the high speed supernatant with 0.5 ml of Ni-NTA-agarose beads (QIAGEN) for 2 h. The beads were washed three times with lysis buffer supplemented with 25 mM imidazole and 1 mM ATP, and protein was eluted with lysis buffer 1 200 mM imidazole and 1 mM ATP. Protein was concentrated by centrifuging the protein in a Millipore-4 concentrator.

EXAMPLE 6

GST Binding Assay

In this Example, GST binding assays conducted during the development of the present invention are described. These assays were conducted as previously described (Tai et al., Cell 97:877–887 [1999]) with minor modifications.

Briefly, purified GST, GST-KLC1 and GST-KLC2 bound to glutathione agarose beads were incubated with 10 μg of indicated purified fusion protein in 150 μl Buffer B (20 mM Tris-Cl, pH 7.5, 50 mM KCl, 100 mM NaCl, 2 mM $CaCl_2$, 2 mM $MgCl_2$, 5 mM DTT, 1% BSA, and protease inhibitors) for 1 hr at 4° C. For the antibody inhibition experiments, the antibody was pre-bound to the beads for 1 hr at 4° C. and then incubated for 1 hr with the indicated protein. The unbound protein (in 150 μl total volume) was saved, and the beads were washed three times with Buffer B. Bound proteins were eluted with 50 μl of elution buffer (50 mM glutathione, 50 mM Tris-Cl, pH 8.0). The bound (50 μl) and unbound (50 μl, i.e., one-third of total volume) proteins were then analyzed by SDS-PAGE followed by Western blotting.

In addition, the binding of APP-GFP or GFP alone to either GST-KLC1 or GST using four other buffers than Buffer B, namely (1) Buffer B without $Ca^{2+}$, (2) Buffer B+500 mM NaCl+1% NP-40, (3) Buffer A from sucrose gradients (10 mM HEPES, pH 7.3, 0.5 mM EGTA, 0.5 mM EGTA, 0.5 mM $MgCl_2$, and (4) PBS (137 mM NaCl, 2.7 mM KCl, 4.3 mM $Na_2HPO_4$ 7 $H_2O$, 1.4 mM $KH_2PO_4$) were tested.

To estimate binding stoichiometry and binding affinity, increasing concentrations of APP-GFP were incubated with known amounts of the GST fusion proteins, and bound APP was separated from free by sedimentation as above. The amounts of bound versus unbound (free) proteins were calculated using quantitative western blots calibrated by multiple exposures of various dilutions of purified proteins to ensure that relative measurements were made in the linear region of detection for each probe. Dissociation constants were estimated from the binding data by nonlinear fitting to the following equation: $PL=\{(P_o+L_o+K_d)-[(P_o+L_o+K_d)^2-4P_oL_o]^{1/2}\}/2$ using GraFit 4 software (Erithacus Software), where Po=total KLC, PL=bound APP-KLC, Lo=total APP, and Kd=dissociation constant for the APP-KLC complex. This explicit quadratic equation was used instead of more commonly used Scatchard analyses, because the standard Scatchard equation, PL=Po−Kd*(PL/L), assumes that ligand concentration does not become significantly depleted as a result of ligand binding. Such an assumption could not be made in the experimental procedures described herein.

To test for direct interactions between the cytoplasmic C-terminal domain of APP and KLC, in vitro binding assays using GST fusion proteins were conducted. The results are shown in FIG. 5, Panel A. GST fused to full-length KLC1 (GST-KLC1) or full-length KLC2 (GST-KLC2) was incubated with a protein consisting of the C-terminal tail of APP fused to GFP (APP-GFP). APP-GFP bound to both GST-KLC1 and GST-KLC2 but not to GST alone. In addition, the GST-KLC1 and GST-KLC2 proteins also bound to an overlapping region of the C-terminal stalk of KIF5B (KIF5B-His) as previously reported (Diefenbach et al., Biochem., 37:16663–16670 [1998]; and Gauger and Goldstein, [1993], supra). In contrast, the C-terminal tail of the kinesin-II subunit, KIF3A (KIF3A-His) or another kinesin-like motor, KIF21A, or GFP alone did not bind GST-KLC1 and GST-KLC2. In addition, the binding of APP-GFP to GST-KLC1 was also tested using five different buffer conditions including high salt concentrations as discussed above. APP-GFP was found to bind to GST-KLC1, but not to GST alone whereas GFP alone did not bind to either GST fusion protein under any of the five tested conditions.

To estimate the binding stoichiometry and binding affinity of APP for KLC, binding experiments were conducted over a wide range of APP-GFP concentrations. The results of these experiments are shown in FIG. 5, Panels B and C). Addition of increasing amounts of APP resulted in saturable binding to KLC with a stoichiometry of 2 APP per 1 KLC. The apparent $K_d$ for binding of APP estimated by curve-fitting was found to be approximately 18+/−4 nM for KLC1 and 16+/−3 nM for KLC2. Thus, these results indicated that the C-terminus of APP can interact directly with KLC with a high affinity.

To examine if the N-terminal domain of KLC or the TPR domain of KLC was responsible for the interaction of APP with KLC, experiments were conducted to test whether the binding of APP-GFP to GST-KLC1 or GST-KLC2 could be inhibited by monoclonal antibodies that recognize either of the two domains. The results of these experiments are shown in FIG. 5, Panel D. The monoclonal antibody 63–90 recognizes an epitope within the N-terminal 50 amino acids of KLC whereas the monoclonal antibody KLC-A11 recognizes the TPR domains of KLC (Stenoien and Brady, [1997], supra); both the antibodies are $IgG_1$ isotypes. Addition of the KLC-A11 antibody inhibited the binding of APP-GFP to both GST-KLC1 and GST KLC2 (See, FIG. 5, Panel D). In contrast, addition of the isotype-matched monoclonal antibody 63–90 did not affect the binding.

To test directly if the C-terminus of APP interacts with the TPR domains of KLC, GST pull-down assays were conducted using GST fusion proteins of KLC1 that contained either the TPR domains (GST-TPR) or only the N-terminal coiled-coil region (GST-CC) (See, FIG. 5, Panel E). Purified APP-GFP protein bound to GST-TPR and not to GST-CC or to GST alone. In contrast, a KIF5B construct that contains part of a region previously found to bind to KLC (Diefenbach et al., [1998], supra; and Gauger and Goldstein, [1993], supra) bound to GST-CC, and not to GST-TPR. GFP alone did not bind to any of the GST fusion proteins. Thus, these results demonstrate that the C-terminus of APP directly binds to the TPR domains of KLC.

EXAMPLE 7

Axonal Transport in Sciatic Nerves

In this Example, experiments conducted to investigate axonal transport in sciatic nerves are described. Sciatic nerves from wild-type and KLC1 mutant mice which were littermates (See, Rahman et al., [1999], supra) were dissected and homogenized in NP-40 lysis buffer, and then spun at 3,000×g and the supernatant collected. Equal amounts of protein were analyzed on SDS-PAGE followed by quantitative Western blotting.

Sciatic ligation experiments were done as previously described (Hanlon et al., 1997). Briefly, one sciatic nerve from each of four wild-type or four mutant KLC1 mice were ligated approximately in the middle; the other nerve was left as an unligated control. Six hours after the ligation, animals were sacrificed and the proximal and distal halves of the nerve flanking the ligature were dissected, pooled and homogenized as described above; the unligated nerve was treated similarly. The protein concentration was measured and equal amounts of protein loaded onto SDS-PAGE gels and analyzed by Western analyses.

In order to test the in vivo significance of the formation of a complex between APP and kinesin-I, the amount of APP present in sciatic nerves in wild-type and mutant KLC1 mice was compared. These results are shown in FIG. 6, Panel A. Since sciatic nerve is composed of sensory and motor neuron axons, some Schwann cell material, but not neuronal cell bodies, this measurement gave an initial estimate of axonal content of APP. Although the total amount and size of APP in brain extracts from the KLC1 mutant mice was normal (See e.g., FIG. 3, HSS), the amount of APP present in sciatic nerves of KLC1 mutants was significantly reduced compared to wildtype, when the sciatic extracts were probed with the APP antibody 22C11 (See, FIG. 6). In the KLC1 mutant, smaller molecular weight bands were sometimes observed in the Western blots with APP, which could be degraded or incorrectly processed APP fragments; the reduction seen in the KLC1 mutant in the bar graph includes these fragments. Since there is the possibility that the APP antibody 22C11 could cross-react with proteins related to APP such as APLP1 or APLP2 (De Strooper and Annaert, [2000], supra), immunoblotting was also conducted with the monoclonal antibody 4G8, which recognizes amino acids 17–24 of the amyloid-beta domain in APP, and thus does not cross-react with APLP1 or APLP2. Immunoblotting with 4G8 also gave the same result (i.e., there is a significant decrease in the amount of APP that is present in the sciatic nerves of the KLC1 mutant).

In addition, the sciatic nerve extracts were probed for synaptic vesicle markers and other transported membrane proteins. The relative amounts of synaptophysin and synaptotagmin, which are pre-synaptic cargoes likely to be transported by a different kinesin-like motor, UNC104/KIF1A (Okada et al., [1995], supra; Otsuka et al., [1991], supra; and Yonekawa et al., [1998], supra) were unchanged in KLC1 mutants compared to wild-type, indicating that cargoes of other motor proteins are unaffected. Strikingly, a significant decrease was observed in the amount of a previously proposed kinesin-I cargo, GAP43, a neuronal membrane protein whose transport into axons was previously shown to be inhibited in cultured hippocampal neurons treated with KHC anti-sense oligonucleotides (Ferreira et al., J. Cell Biol., 117:595–606 [1992]). These results indicate that there is decreased axonal transport of APP and GAP43 in the KLC1 mutant, whereas bulk biosynthesis and axonal transport of other non-kinesin-I membrane cargoes is unaffected.

Further, to assess directly if the APP assayed by Western blot of whole sciatic nerves reflects the anterograde axonal transport population, and to confirm that axonal transport of APP is reduced in the KLC1 mutant, biochemical analyses of sciatic nerve ligation experiments were conducted. The results of these experiments are shown in FIG. 6, Panel B. Sciatic nerves were ligated in the middle for 6 hours and then proximal and distal halves relative to the point of ligature were assayed for accumulation or depletion of APP and various marker proteins previously shown to be part of anterograde, retrograde, or slowly moving populations (reviewed in Goldstein and Yang, Ann. Rev. Neurosci., 23:39–72 [2000]). As previously reported, the anterograde motor kinesin-I (detected using KIF5B antibody) exhibited massive accumulation on the proximal side of the ligature and depletes on the distal side. The retrograde motor dynein (detected with the dynein intermediate chain antibody) only modestly accumulated or remained the same in the proximal and distal halves of the ligation. The slow transport marker tubulin exhibited equal abundance in proximal and distal halves of ligated and control nerves as expected. In wild-type mice, a substantial increase of APP on the proximal side after a six hour ligation accompanied by a striking and reproducible depletion in the distal half was observed (data shown for antibody 22C11; comparable data were obtained with 4G8, but are not shown). Similarly, a significant increase of GAP43 on the proximal side accompanied by depletion in the distal side was also observed.

These data indicate that most of the APP (and GAP43) detected by Western blot of whole sciatic nerve is part of the moving fraction, while only a small fraction of the APP is not moving or is contributed from non-neuronal Schwann cells present in sciatic nerves. Analysis of comparable sciatic ligation experiments in KLC1 mutant mice revealed a significant decrease in the amount of APP that accumulated on the proximal side after ligation and an apparently smaller relative depletion on the distal side compared to wild-type. The control markers tubulin, dynein, KIF5B, and synaptotagmin had the same behavior in the mutant as in wild-type suggesting a selective defect as expected. Although an understanding of the mechanism(s) is not necessary in order to use the present invention, it is contemplated that the residual transport of APP observed in the KLC1 mutant is mediated by the remaining KLC2, which is also known to be expressed in sciatic nerve axons (See, Rahman et al., [1999], supra). However, taken together, these results indicate that the axonal transport of APP is greatly decreased in a KLC1 mutant.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art and/or related fields are intended to be within the scope of the following Claims.

We claim:

1. A method for identifying modulators of transport of amyloid precursor protein comprising the steps of:
   a) providing:
      i) kinesin-I,
      ii) amyloid precursor protein, and
      iii) a test compound suspected of having modulating activity;
   b) combining said kinesin-1, said amyloid precursor protein, and said test compound under conditions such that said kinesin-I and said amyloid precursor protein will bind to produce a kinesin-I/amyloid precursor protein complex; and
   c) detecting modulation in the binding of said kinesin-I to said amyloid precursor protein in the presence of said test compound compared to in the absence of said test compound, thereby identifying said test compound as a modulator of transport of amyloid precursor protein.

2. The method of claim 1, wherein the TPR domain of the light chain of said kinesin-I interacts with said amyloid precursor protein.

3. The method of claim 1, wherein said binding of said kinesin-I to said amyloid precursor protein is inhibited in the presence of said test compound compared to in the absence of said test compound.

4. The niethod of claim 1, wherein the binding of said kinesin-I to said amyloid precursor protein is enhanced in the presence of said test compound compared to in the absence of said test compound.

5. The method of claim 1, wherein said detecting of the binding of said kiiiesin-I to said amyloid precursor protein comprises a detecting method selected from the group consisting of co-immunoprecipitation methods, co-immunoprecipitation followed by Western blotting, sucrose gradient centrifugation, microtubule binding assays, column chromatography methods, gel overlays, ATPase assays, and surface plasmon resonance.

6. The method of claim 5, wherein said detecting method comprises a microtubule binding assay.

7. The method of claim 1, wherein said detecting method is biochemical.

8. The method of claim 1, wherein said combining is conducted within a cell.

9. The method of claim 1, wherein said combining is conducted within an animal.

10. The method of claim 5, wherein said detecting method comprises a co-immunoprecipitation method.

11. The method of claim 10, wherein said detecting method further comprises Western blotting.

12. The method of claim 5, wherein said detecting method comprises sucrose gradient centrifugation.

13. The method of claim 5, wherein said detecting method comprises an ATPase assay.

* * * * *

UNITED STATES PATENT AND TRADEMARK OFFICE
CERTIFICATE OF CORRECTION

PATENT NO. : 6,673,332 B1
DATED : January 6, 2004
INVENTOR(S) : Goldstein et al.

It is certified that error appears in the above-identified patent and that said Letters Patent is hereby corrected as shown below:

Column 40,
Line 11, please delete "niethod" and insert -- method --.
Line 16, please delete "kiiesin-I" and insert -- kinesin-I --.

Signed and Sealed this

Ninth Day of March, 2004

JON W. DUDAS
*Acting Director of the United States Patent and Trademark Office*